(12) United States Patent
Sadowsky et al.

(10) Patent No.: US 8,367,389 B2
(45) Date of Patent: Feb. 5, 2013

(54) METHODS, COMPOSITIONS AND DEVICES UTILIZING STRUCTURALLY STABLE CYANURIC ACID HYDROLASE

(75) Inventors: Michael J. Sadowsky, St. Paul, MN (US); Jennifer L. Seffernick, St. Paul, MN (US); Lawrence P. Wackett, St. Paul, MN (US)

(73) Assignee: Regents of the University of Minnesota, Saint Paul, MN (US)

( * ) Notice: Subject to any disclaimer, the term of this patent is extended or adjusted under 35 U.S.C. 154(b) by 292 days.

(21) Appl. No.: 12/879,903

(22) Filed: Sep. 10, 2010

(65) Prior Publication Data
US 2011/0127208 A1 Jun. 2, 2011

Related U.S. Application Data

(60) Provisional application No. 61/241,797, filed on Sep. 11, 2009.

(51) Int. Cl.
*C12N 9/14* (2006.01)
(52) U.S. Cl. ........................... 435/195; 435/212
(58) Field of Classification Search ............. 435/195, 435/212
See application file for complete search history.

(56) References Cited

U.S. PATENT DOCUMENTS

| | | | |
|---|---|---|---|
| 4,071,409 | A | 1/1978 | Messing et al. |
| 4,090,919 | A | 5/1978 | Chibata et al. |
| 4,258,133 | A | 3/1981 | Mirabel et al. |
| 4,532,040 | A | 7/1985 | Meeks et al. |
| 4,888,285 | A | 12/1989 | Nishimura et al. |
| 4,935,116 | A | 6/1990 | LeMire |
| 5,055,183 | A | 10/1991 | Buchan |
| 5,177,013 | A | 1/1993 | Usui et al. |
| 5,310,469 | A | 5/1994 | Cunningham et al. |
| 5,478,467 | A | 12/1995 | LeMire et al. |
| 5,855,777 | A | 1/1999 | Bachand et al. |
| 5,980,761 | A | 11/1999 | Boissie et al. |
| 5,998,183 | A | 12/1999 | LeFevre et al. |
| 6,257,242 | B1 | 7/2001 | Stavridis |
| 6,325,929 | B1 | 12/2001 | Bassett |
| 6,673,582 | B2 | 1/2004 | McTavish |
| 6,905,733 | B2 | 6/2005 | Russell et al. |
| 6,987,079 | B2 | 1/2006 | Wormsbecher |
| 2003/0096383 | A1 | 5/2003 | Shimizu et al. |

FOREIGN PATENT DOCUMENTS
WO WO 2007/107981 A2 9/2007

OTHER PUBLICATIONS

Soong et al. J. Biol. Chem. (2002) 227(9): 7061-7068.*
Eaton et al. J. Bacteriol. (1991) 173(3): 1363-1366.*
Fruchey et al. Appl. Environ. Microbiol. (2003): 69(6): 3653-3657.*
Pierce et al. Environ. Microbiol. (Oct. 2008) 10(10): 2550-2573.*
EMBL printout barbiturase (Morlle thermoacetica ATCC 39073) Genbank: ABC20412.1 http://www.ncbi.nlm.nih.gov/protein/83573860 downloaded Sep. 21, 2012.*
Cantú et al., "An HPLC Method with UV Detection, pH Control, and Reductive Ascorbic Acid for Cyanuric Acid Analysis in Water", *Anal. Chem.*, 72, 5820-5828 (2000).
de Souza et al, "Atrazine Chlorohydrolase from Pseudomonas sp. ADP: Gene Sequence, Enzyme Purification and Protein Characterization", *J. Bacteriol.*, 178, 4894-4900, Supp. p. 695 (1996).
Devers et al., "Detection and Organization of Atrazine-degrading Genetic Potential of Seventeen Bacterial Isolates Belonging to Divergent Taxa Indicate a Recent Common Origin of Their Catabolic Functions", *FEMS Microbiol Lett.*, 273, 78-86 (2007).
Fontaine et al., "A New Type of Glucose Fermentation by Clostridium Thermoaceticum", *J. Bacteriol.*, 43, 701-715 (1942).
Hennig86, "A PC-DOS Program for Phylogenetic Analysis", *Cladistics*, 5, 163-166 (1989).
Karns, J.S., "Gene Sequence and Properties of an s-triazine ring-cleavage enzyme from *Pseudomonas* sp. Strain NRRLB-12227", *Appl. Environ. Microbiol.*, 65, 3512-3517 (1999).
Li et al., "Thermostable Cyanuric Acid Hydrolase from Moorella Thermoacetica ATCC 39073", *Applied and Environmental Microbiology*, vol. 75, No. 22, 6986-6991 (2009).
Marsili et al, "Microbial Biofilm Voltammetry: Direct Electrochemical Characterization of Catalytic Electrode-Attached Biofilms", *Appl Environ Microbiol.*, 74, 7329-7337 (2008).
Puschner et al., "Assessment of Melamine and Cyanuric Acid in Cats", *J Vet Diagn Invest* 19, 616-624 (2007).
Seffernick et al., "Hydroxyatrazine N-ethylaminohydrolase (AtzB): an amidohydrolase superfamily enzyme catalyzing deamination and dechlorinations", *J. Bacteriol.*, 189, 6989-6997 (2007).
Seffernick et al., "Atrazine Chlorohydrolase from *Pseudomonas* sp. Strain ADP is a metalloenzyme", *Biochemistry*, 41, 14430-14437 (2002).
Shapir et al., "Purification, Substrate Range, and Metal Center of AtzC: the N-isopropylammelide aminohydrolase involved in Bacterial Atrazine Metabolism", *J. Bacteriol.*, 184, 5376-5384 (2002).
Shapir et al., "TrzN from Arthrobacter Aurescens TC1 is a Zinc Amidohydrolase", *J Bacteriol.*, 188, 5859-5864 (2006).
Smith et al., "Cooperative Catabolic Pathways Within an Atrazine-degrading Enrichment Culture Isolated from Soil", *FEMS Microbiol Ecol.*, 53, 265-273 (2005).
Thompson et al., "CLUSTAL W: Improving the Sensitivity of Progressive Multiple Sequence Alignment Through Sequence Weighting, Position-Specific Gap Penalties and Weight Matrix Choice", *Nucleic Acids Res.*, 22, 4673-4680 (1994).
van der Maarel et al., "Demethylation of Dimethylsulfoniopropionate to 3-S-methylmercaptopropionate by marine sulfate-reducing bacteria", *Appl Environ Microbiol.*, 62, 3927-3984 (1996).
Yan-A-X. et al., "Recent Progress on Immobilization of Enzymes on Molecular Sieves for Reactions in Organic Solvents", *Applied Biochemistry and Biotechnology*, vol. 101(2), 113-130(18) (2002).

* cited by examiner

*Primary Examiner* — Susan Hanley
(74) *Attorney, Agent, or Firm* — Viksnins Harris & Padys PLLP

(57) ABSTRACT

The present invention relates to stable cyanuric acid hydrolase enzymes, compositions, and devices for use in the treatment of a liquid, such as water. The present invention also relates to methods of using these enzymes, compositions and devices for the treatment of a liquid, such as water.

17 Claims, 5 Drawing Sheets

FIG. 2. Protein tree of cyanuric acid hydrolases and their close relatives.

FIG. 3.
A. Substrates
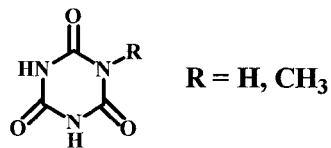
R = H, CH₃
B. Not Substrates
Barbituric acid derivatives
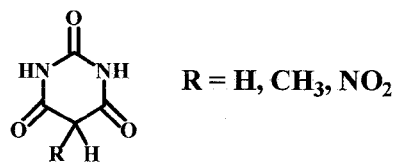
R = H, CH₃, NO₂
Pyrimidines
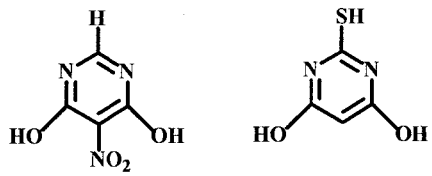
***s*-Triazines**
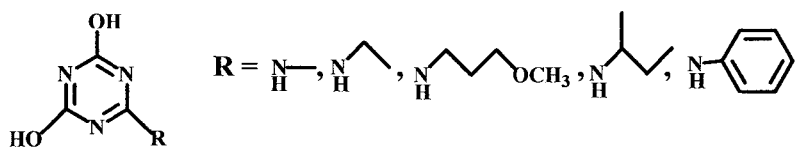
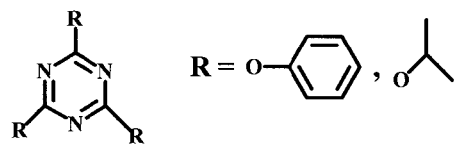
R = H, CH₃
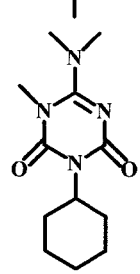

SEQUENCE LISTING

<160> NUMBER OF SEQ ID NOS: 18

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
gcgaattcca tatgcaaaaa gttgaagtct t                                      31

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
gccaagcttc tacaccctgg caataacag                                         29

<210> SEQ ID NO 3
<211> LENGTH: 367
<212> TYPE: PRT
<213> ORGANISM: Moorella thermoacetica

<400> SEQUENCE: 3

Met Gln Lys Val Glu Val Phe Arg Ile Pro Thr Ala Ser Pro Asp Asp
1               5                   10                  15

Ile Ser Gly Leu Ala Thr Leu Ile Asp Ser Gly Lys Ile Asn Pro Ala
            20                  25                  30

Glu Ile Val Ala Ile Leu Gly Lys Thr Glu Gly Asn Gly Cys Val Asn
        35                  40                  45

Asp Phe Thr Arg Gly Phe Ala Thr Gln Ser Leu Ala Met Tyr Leu Ala
    50                  55                  60

Glu Lys Leu Gly Ile Ser Arg Glu Glu Val Val Lys Val Ala Phe
65                  70                  75                  80

Ile Met Ser Gly Gly Thr Glu Gly Val Met Thr Pro His Ile Thr Val
                85                  90                  95

Phe Val Arg Lys Asp Val Gln Glu Pro Ala Lys Pro Gly Lys Arg Leu
            100                 105                 110

Ala Val Gly Val Ala Phe Thr Arg Asp Phe Leu Pro Glu Glu Leu Gly
        115                 120                 125

Arg Met Glu Gln Val Asn Glu Val Ala Arg Ala Val Lys Glu Ala Met
    130                 135                 140

Lys Asp Ala Gln Ile Asp Asp Pro Arg Asp Val His Phe Val Gln Ile
145                 150                 155                 160

Lys Cys Pro Leu Leu Thr Ala Glu Arg Ile Glu Asp Ala Lys Arg Arg
                165                 170                 175

Gly Lys Asp Val Val Val Asn Asp Thr Tyr Lys Ser Met Ala Tyr Ser
            180                 185                 190

Arg Gly Ala Ser Ala Leu Gly Val Ala Leu Ala Leu Gly Glu Ile Ser
        195                 200                 205

Ala Asp Lys Ile Ser Asn Glu Ala Ile Cys His Asp Trp Asn Leu Tyr
    210                 215                 220

Ser Ser Val Ala Ser Thr Ser Ala Gly Val Glu Leu Leu Asn Asp Glu
225                 230                 235                 240

Ile Ile Val Val Gly Asn Ser Thr Asn Ser Ala Ser Asp Leu Val Ile
                245                 250                 255

Gly His Ser Val Met Lys Asp Ala Ile Asp Ala Asp Ala Val Arg Ala
            260                 265                 270

Ala Leu Lys Asp Ala Gly Leu Lys Phe Asp Cys Cys Pro Pro Ala Glu
        275                 280                 285

Glu Leu Ala Lys Ile Val Asn Val Leu Ala Lys Ala Glu Ala Ala Ser
    290                 295                 300

Ser Gly Thr Val Arg Gly Arg Arg Asn Thr Met Leu Asp Ser Asp
305                 310                 315                 320

Ile Asn His Thr Arg Ser Ala Arg Ala Val Val Asn Ala Val Ile Ala
                325                 330                 335

Ser Val Val Gly Asp Pro Met Val Tyr Val Ser Gly Gly Ala Glu His
            340                 345                 350

Gln Gly Pro Asp Gly Gly Pro Ile Ala Val Ile Ala Arg Val
        355                 360                 365

<210> SEQ ID NO 4
<211> LENGTH: 1104
<212> TYPE: DNA
<213> ORGANISM: Moorella thermoacetica

<400> SEQUENCE: 4
ctacaccctg gcaataacag caattgggcc accgccatca ggcccttgat gctctgcacc      60
accggaaacg tagaccatag gatctcctac cacgctggca ataacagcat ttactactgc     120
tcgcgccgag cgggtatgat tgatatcaga gtcatcaagc atcgtgttac gcctacccct     180
tactgtacca gaagatgcgg cctcagcctt ggccagtaca ttaacgatct tagcaagctc     240
ttctgctggc gggcaacaat caaattttaa accggcatct ttaagggcag cacgtactgc     300
atcagcgtca atggcatcct tcataacaga gtggcctata accaaatcac tggcactatt     360
ggtagagttt cctactacga taatttcgtc attaagaagt tcaaccccccg ctgacgtcga     420 agccacacta gagtagagat tccagtcatg acaaattgct tcgttgctaa tcttatccgc     480
agatatctcg cccagtgcga gggccactcc gagagctgag gcgccacgtg agtaagccat     540
tgatttataa gtgtcattta ccacaacatc tttcccgcgt cgcttggcat cctcaattct     600
ttcagcagtc aaaagcgggc actttatctg aacaaagtga acgtcgcggg gatcatctat     660
ttgggcgtct ttcatagcct cttttacagc tcgagccact tcgtttacct gttccatccg     720
gcccaattct tccggcagaa agtcccgcgt aaaagctacg cctactgcca agcgctttcc     780
tggcttagct ggttcctgga catctttcg gacaaagaca gtaatgtgcg gcgtcataac     840
accctcagta ccgcctgaca ttataaacgc aactttttt acaacttctt cgcggcttat     900
tcccaatttt tctgctagat acattgctag agattgggta gcaaaaccgc gagtaaaatc     960
gttaacacaa ccattacctt ccgtcttgcc cagaatagct acaatttcag ccggattaat    1020
cttccctgag tcaatcaaag tagccaaccc gctgatatca tcaggtgagg ctgttgggat    1080
acgaaagact tcaactttt gcat                                             1104

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic

```
              peptide
<220> FEATURE:
<221> NAME/KEY: MOD_RES
<222> LOCATION: (1)..(1)
<223> OTHER INFORMATION: Gly or Ala
<220> FEATURE:
<221> NAME/KEY: MOD_RES
<222> LOCATION: (8)..(8)
<223> OTHER INFORMATION: Cys or Gly
<220> FEATURE:
<221> NAME/KEY: MOD_RES
<222> LOCATION: (12)..(12)
<223> OTHER INFORMATION: Tyr or Phe
<220> FEATURE:
<221> NAME/KEY: MOD_RES
<222> LOCATION: (13)..(13)
<223> OTHER INFORMATION: Thr or Ser

<400> SEQUENCE: 5

Xaa Lys Thr Glu Gly Asn Gly Xaa Val Asn Asp Xaa Xaa Arg
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Val or Ile
<220> FEATURE:
<221> NAME/KEY: MOD_RES
<222> LOCATION: (9)..(9)
<223> OTHER INFORMATION: Val, Ala, or Gly
<220> FEATURE:
<221> NAME/KEY: MOD_RES
<222> LOCATION: (10)..(10)
<223> OTHER INFORMATION: Leu or Met
<220> FEATURE:
<221> NAME/KEY: MOD_RES
<222> LOCATION: (11)..(11)
<223> OTHER INFORMATION: Ser, Ala, or Thr

<400> SEQUENCE: 6

Xaa Met Ser Gly Gly Thr Glu Gly Xaa Xaa Xaa Pro His
1               5                   10

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Glu, His, Asp, or Ala
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Arg or Thr

<400> SEQUENCE: 7

Glu Xaa Xaa Gly Xaa
1               5
```

```
<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp or Gln
<220> FEATURE:
<221> NAME/KEY: MOD_RES
<222> LOCATION: (2)..(2)
<223> OTHER INFORMATION: Leu, Val, or Ala
<220> FEATURE:
<221> NAME/KEY: MOD_RES
<222> LOCATION: (4)..(4)
<223> OTHER INFORMATION: Phe, Tyr, or Leu
<220> FEATURE:
<221> NAME/KEY: MOD_RES
<222> LOCATION: (7)..(7)
<223> OTHER INFORMATION: Val or Ile

<400> SEQUENCE: 8

Xaa Xaa His Xaa Val Gln Xaa Lys Cys Pro Leu Leu Thr
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Gly, Ala, or Ser
<220> FEATURE:
<221> NAME/KEY: MOD_RES
<222> LOCATION: (4)..(4)
<223> OTHER INFORMATION: Tyr, Phe, or Leu
<220> FEATURE:
<221> NAME/KEY: MOD_RES
<222> LOCATION: (5)..(5)
<223> OTHER INFORMATION: Ser or Asn
<220> FEATURE:
<221> NAME/KEY: MOD_RES
<222> LOCATION: (7)..(7)
<223> OTHER INFORMATION: Gly or Arg
<220> FEATURE:
<221> NAME/KEY: MOD_RES
<222> LOCATION: (9)..(9)
<223> OTHER INFORMATION: Ser or Ala

<400> SEQUENCE: 9

Ser Met Xaa Xaa Xaa Arg Xaa Ala Xaa Ala Leu Gly
1               5                   10

<210> SEQ ID NO 10
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser, Ala, or Gly
<220> FEATURE:
<221> NAME/KEY: MOD_RES
<222> LOCATION: (2)..(2)
<223> OTHER INFORMATION: Ala, Thr, or Cys
<220> FEATURE:
```

```
<221> NAME/KEY: MOD_RES
<222> LOCATION: (4)..(4)
<223> OTHER INFORMATION: Ser, Ala, or Gly
<220> FEATURE:
<221> NAME/KEY: MOD_RES
<222> LOCATION: (6)..(6)
<223> OTHER INFORMATION: Ile, Val, Gly, or Ser
<220> FEATURE:
<221> NAME/KEY: MOD_RES
<222> LOCATION: (9)..(10)
<223> OTHER INFORMATION: Any amino acid
<220> FEATURE:
<221> NAME/KEY: MOD_RES
<222> LOCATION: (11)..(11)
<223> OTHER INFORMATION: Asn, Asp, Cys, or His
<220> FEATURE:
<221> NAME/KEY: MOD_RES
<222> LOCATION: (12)..(12)
<223> OTHER INFORMATION: Val or Glu
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(18)
<223> OTHER INFORMATION: Met or Asn
<220> FEATURE:
<221> NAME/KEY: MOD_RES
<222> LOCATION: (19)..(19)
<223> OTHER INFORMATION: Ser or Ala
<220> FEATURE:
<221> NAME/KEY: MOD_RES
<222> LOCATION: (20)..(21)
<223> OTHER INFORMATION: Any amino acid
<220> FEATURE:
<221> NAME/KEY: MOD_RES
<222> LOCATION: (22)..(22)
<223> OTHER INFORMATION: Ser, Ala, or Trp

<400> SEQUENCE: 10

Xaa Xaa Ser Xaa Gly Xaa Glu Leu Xaa Xaa Xaa Xaa Xaa Xaa Xaa Xaa
1               5                   10                  15

Gly Xaa Xaa Xaa Xaa Xaa
            20

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Val or Glu
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(7)
<223> OTHER INFORMATION: Ala or Gly
<220> FEATURE:
<221> NAME/KEY: MOD_RES
<222> LOCATION: (8)..(8)
<223> OTHER INFORMATION: Ile or Met

<400> SEQUENCE: 11

His Xaa Xaa Met Xaa Asp Xaa Xaa Asp
```

-continued 1               5

<210> SEQ ID NO 12
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Ala Glu
1

<210> SEQ ID NO 13
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or Asp
<220> FEATURE:
<221> NAME/KEY: MOD_RES
<222> LOCATION: (2)..(2)
<223> OTHER INFORMATION: Gly or Asn
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: His or Asn
<220> FEATURE:
<221> NAME/KEY: MOD_RES
<222> LOCATION: (6)..(6)
<223> OTHER INFORMATION: Thr or Ile
<220> FEATURE:
<221> NAME/KEY: MOD_RES
<222> LOCATION: (8)..(8)
<223> OTHER INFORMATION: Leu, His, or Asn
<220> FEATURE:
<221> NAME/KEY: MOD_RES
<222> LOCATION: (9)..(9)
<223> OTHER INFORMATION: Ser, Thr, Asp, or Glu
<220> FEATURE:
<221> NAME/KEY: MOD_RES
<222> LOCATION: (11)..(11)
<223> OTHER INFORMATION: Ser or Thr
<220> FEATURE:
<221> NAME/KEY: MOD_RES
<222> LOCATION: (13)..(13)
<223> OTHER INFORMATION: Ile or Val
<220> FEATURE:
<221> NAME/KEY: MOD_RES
<222> LOCATION: (14)..(14)
<223> OTHER INFORMATION: Asn, Ser, or Ala
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (18)..(18)
<223> OTHER INFORMATION: His or Ser
<220> FEATURE:
<221> NAME/KEY: MOD_RES
<222> LOCATION: (21)..(21)
<223> OTHER INFORMATION: Ala or Gly

<400> SEQUENCE: 13

Xaa Xaa Xaa Arg Xaa Xaa Met Xaa Xaa Asp Xaa Asp Xaa Xaa Xaa Thr

```
1               5                  10                  15
Arg Xaa Ala Arg Xaa
            20
```

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Val, Ile, or Leu
<220> FEATURE:
<221> NAME/KEY: MOD_RES
<222> LOCATION: (2)..(2)
<223> OTHER INFORMATION: Phe or Tyr
<220> FEATURE:
<221> NAME/KEY: MOD_RES
<222> LOCATION: (7)..(7)
<223> OTHER INFORMATION: Ser, Ala, or Gly
<220> FEATURE:
<221> NAME/KEY: MOD_RES
<222> LOCATION: (13)..(13)
<223> OTHER INFORMATION: Ala, Asp, or Pro

<400> SEQUENCE: 14

```
Xaa Xaa Val Ser Gly Gly Xaa Glu His Gln Gly Pro Xaa Gly Gly Gly
1               5                  10                  15
Pro
```

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Cys, Gly, or Leu
<220> FEATURE:
<221> NAME/KEY: MOD_RES
<222> LOCATION: (7)..(7)
<223> OTHER INFORMATION: Val, Met, or Ala
<220> FEATURE:
<221> NAME/KEY: MOD_RES
<222> LOCATION: (10)..(10)
<223> OTHER INFORMATION: Tyr or Phe
<220> FEATURE:
<221> NAME/KEY: MOD_RES
<222> LOCATION: (11)..(11)
<223> OTHER INFORMATION: Thr or Ser

<400> SEQUENCE: 15

```
Thr Glu Gly Asn Gly Xaa Xaa Asn Asp Xaa Xaa Arg
1               5                  10
```

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Thr Glu Gly Asn Gly Cys Val Asn Asp Phe Thr Arg
1               5                  10
```

```
<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Met, Phe, Leu, or Ile
<220> FEATURE:
<221> NAME/KEY: MOD_RES
<222> LOCATION: (2)..(2)
<223> OTHER INFORMATION: Val, Ile, or Met
<220> FEATURE:
<221> NAME/KEY: MOD_RES
<222> LOCATION: (3)..(3)
<223> OTHER INFORMATION: Met, Phe, or Trp
<220> FEATURE:
<221> NAME/KEY: MOD_RES
<222> LOCATION: (7)..(7)
<223> OTHER INFORMATION: Asp, Glu, Gly, or Pro
<220> FEATURE:
<221> NAME/KEY: MOD_RES
<222> LOCATION: (9)..(9)
<223> OTHER INFORMATION: Val, Ile, Leu, Gly, or Ala
<220> FEATURE:
<221> NAME/KEY: MOD_RES
<222> LOCATION: (10)..(10)
<223> OTHER INFORMATION: Leu, Ile, Met, or Ala
<220> FEATURE:
<221> NAME/KEY: MOD_RES
<222> LOCATION: (11)..(11)
<223> OTHER INFORMATION: Ser, Thr, Ala, or Cys
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (15)..(15)
<223> OTHER INFORMATION: Thr, Ile, Leu, or Ser
<220> FEATURE:
<221> NAME/KEY: MOD_RES
<222> LOCATION: (16)..(16)
<223> OTHER INFORMATION: Val, Ile, or Leu
<220> FEATURE:
<221> NAME/KEY: MOD_RES
<222> LOCATION: (17)..(17)
<223> OTHER INFORMATION: Phe, Ile, or Val

<400> SEQUENCE: 17

Xaa Xaa Xaa Ser Gly Gly Xaa Gly Xaa Xaa Xaa Pro His Xaa Xaa Xaa
1               5                   10                  15

Xaa

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Phe Ile Met Ser Gly Gly Glu Gly Val Met Thr Pro His Thr Val Phe
1               5                   10                  15
```

METHODS, COMPOSITIONS AND DEVICES UTILIZING STRUCTURALLY STABLE CYANURIC ACID HYDROLASE

REFERENCE TO RELATED APPLICATIONS

This application claims priority under 35 U.S.C. 119(e) from U.S. Provisional Application Ser. No. 61/241,797 filed Sep. 11, 2009, which is incorporated herein by reference.

SEQUENCE LISTING

The instant application contains a Sequence Listing which has been submitted in ASCII format via EFS-Web and is hereby incorporated by reference in its entirety. Said ASCII copy, created on Jan. 19, 2011, is named 09531291.txt and is 13,619 bytes in size.

BACKGROUND OF THE INVENTION s-Triazine compounds have diverse applications as herbicides, resins, and disinfectants. The s-triazine herbicides, such as atrazine, help promote high-yields and sustainability in agricultural crops.

Melamine, or triamino-s-triazine, is a high volume industrial chemical. Melamine-based polymers have outstanding thermosetting properties, are ideal for their use in kitchen utensils and plates, and as high-pressure laminates such as Formica, and as whiteboards. Di- and tri-chloroinated isocyanuric acids find widespread application as disinfectants, algicides, and bactericides. The chlorinated isocyanuric acids are used in water treatment, in the textile industry as bleaching compounds, and in preventing and curing diseases in husbandry and fisheries. A major use of these compounds is for swimming pool chlorination. They have outstanding performance for maintaining an elevated, stable, chlorine content by dissolving slowly in water, allowing a continuous metered dosing of chlorine.

Degradation of these and other s-triazine compounds results in the production of cyanuric acid (FIG. 1). Cyanuric acid has come under increased scrutiny because of its potential involvement in co-mediating toxicity resulting from the ingestion of melamine (Puschner, B., et al., 2007. *J Vet Diagn Invest* 19:616-24). Recently, melamine has been found in adulterated pet food and baby formula. Melamine and its metabolite cyanuric acid co-crystallize at low concentrations and are implicated in acute renal failure in cats that have consumed adulterated food products (Puschner, B., et al., 2007. *J Vet Diagn Invest* 19:616-24). Cyanuric acid degradation is also of interest from the perspective of environmental remediation. The use of di- or tri-chloroisocyanuric acid in pool water results in spontaneous chemical dechlorination that disinfects the water, but also produces as a by-product large amounts of cyanuric acid. High levels of cyanuric acid perturb the equilibrium of dissolution of chloro-cyanuric acids preventing dechlorination by additional chlorinated isocyanuric acid. If this happens, disinfection is not achieved. As a result, swimming pools must be emptied and refilled, using water and causing discharge issues. It would be desirable to remediate pool water in situ, maintaining disinfection ability, conserving water, saving money and extending pool water use.

SUMMARY OF THE INVENTION

The present invention provides an isolated or purified structurally stable cyanuric acid hydrolase (CAH) enzyme. In certain embodiments, the CAH has a $K_m$ value for cyanuric acid of 25-150 µM. In certain embodiments, the CAH has a $K_m$ value for cyanuric acid of 100-130 µM. In certain embodiments, the CAH has a $k_{cat}$ value for cyanuric acid of 4.8-76 $s^{-1}$. In certain embodiments, the enzyme is thermostable. In certain embodiments, the CAH is thermostable such that the enzyme retains at least 30% (e.g., at least 40%, at least 50%, at least 95%, or any other value between 30% and 100%) enzymatic activity at a temperature above 25° C., and has activity up to 70° C. In certain embodiments, the enzyme is stable when stored at between room temperature and −80° C. (e.g., between 20° C. and −80° C., or any other value in between) for at least 8 weeks. In certain embodiments, the enzyme is stable for at least 1 year. In certain embodiments, the enzyme retains enzymatic activity at a pH of from 5.5 to 10.5. In certain embodiments, the enzyme is from *Moorella thermoacetica*, such as from *Moorella thermoacetica* ATCC 39073.

In certain embodiments, the CAH enzyme contains at least 19 Lys residues. In certain embodiments, the CAH enzyme contains at least 40 Arg and/or Lys residues. In certain embodiments, the CAH enzyme contains at least 50 Asp and/or Glu residues.

In certain embodiments, the CAH enzyme comprises amino acid sequence TEGNG(C/G/L)(V/M/A)ND(Y/F)(T/S)R (SEQ ID NO:15), such as sequence TEGNGCVNDFTR (SEQ ID NO:16). In certain embodiments, the CAH enzyme comprises amino acid sequence (M/F/L/I)(V/I/M)(M/F/W) SGG (D/E/G/P)G(V/I/L/G/A)(L/I/M/A)(S/T/A/C)PHX(T/I/L/S)(V/I/L)(F/I/V) (SEQ ID NO:17), wherein X is any amino acid, such as sequence FIMSGGEGVMTPHTVF (SEQ ID NO:18). In certain embodiments, the enzyme comprises amino acid sequence TEGNG(C/G/L)(V/M/A)ND(Y/F)(T/S)R (SEQ ID NO:15) and amino acid sequence (M/F/L/I)(V/I/M)(M/F/W)SGG (D/E/G/P)G(V/I/L/G/A)(L/I/M/A)(S/T/A/C)PHX(T/I/L/S)(V/I/L)(F/I/V) (SEQ ID NO:17), wherein X is any amino acid. In certain embodiments, the enzyme comprises amino acid sequence TEGNGCVNDFTR (SEQ ID NO:16) and amino acid sequence FIMSGGEGVMTPH-TVF (SEQ ID NO:18).

In certain embodiments, the enzyme is 350-380 amino acids in length. In certain embodiments, the enzyme has a pI of about 5-6.

In certain embodiments, the CAH is SEQ ID NO: 3:

MQKVEVFRIPTASPDDISGLATLIDSGKINPAEIVAILGKTEGNGCVND

FTRGFATQSLAMYLAEKLGISREEVVKKVAFIMSGGTEGVMTPHITVFV

RKDVQEPAKPGKRLAVGVAFTRDFLPEELGRMEQVNEVARAVKEAMKDA

QIDDPRDVHFVQIKCPLLTAERIEDAKRRGKDVVVNDTYKSMAYSRGAS

ALGVALALGEISADKISNEAICHDWNLYSSVASTSAGVELLNDEIIVVG

NSTNSASDLVIGHSVMKDAIDADAVRAALKDAGLKFDCCPPAEELAKIV

NVLAKAEAASSGTVRGRRNTMLDDSDINHTRSARAVVNAVIASVVGDPM

VYVSGGAEHQGPDGGGPIAVIARV.

In certain embodiments, the CAH has an SDS-PAGE protein band corresponding to about 40 kDa. In certain embodiments, the CAH has a specific activity of 12-18 µmol/min/mg with cyanuric acid as substrate and a specific activity of less than 2 µmol/min/mg with barbituric acid as substrate. In certain embodiments, the CAH has a specific activity of 15.7 µmol/min/mg with cyanuric acid as substrate, but does not show detectable activity with barbituric acid. In certain embodiments, the CAH enzyme shows less that 10% detectable activity with barbituric acid as compared to the enzyme's activity with cyanuric acid.

In certain embodiments, the CAH enzyme contains at least 19 Lys residues. In certain embodiments, the CAH enzyme contains at least 40 Arg and/or Lys residues. In certain embodiments, the CAH enzyme contains at least 50 Asp and/or Glu residues.

The present invention provides an isolated or purified nucleic acid molecule comprising SEQ ID NO: 4:

CTACACCCTGGCAATAACAGCAATTGGGCCACCGCCATCAGGCCCTTGA

TGCTCTGCACCACCGGAAACGTAGACCATAGGATCTCCTACCACGCTGG

CAATAACAGCATTTACTACTGCTCGCGCCGAGCGGGTATGATTGATATC

AGAGTCATCAAGCATCGTGTTACGCCTACCCCTTACTGTACCAGAAGAT

GCGGCCTCAGCCTTGGCCAGTACATTAACGATCTTAGCAAGCTCTTCTG

CTGGCGGGCAACAATCAAATTTTAAACCGGCATCTTTAAGGGCAGCACG

TACTGCATCAGCGTCAATGGCATCCTTCATAACAGAGTGGCCTATAACC

AAATCACTGGCACTATTGGTAGAGTTTCCTACTACGATAATTTCGTCAT

TAAGAAGTTCAACCCCCGCTGACGTCGAAGCCACACTAGAGTAGAGATT

CCAGTCATGACAAATTGCTTCGTTGCTAATCTTATCCGCAGATATCTCG

CCCAGTGCGAGGGCCACTCCGAGAGCTGAGGCGCCACGTGAGTAAGCCA

TTGATTTATAAGTGTCATTTACCACAACATCTTTCCCGCGTCGCTTGGC

ATCCTCAATTCTTTCAGCAGTCAAAAGCGGGCACTTTATCTGAACAAAG

TGAACGTCGCGGGATCATCTATTTGGGCGTCTTTCATAGCCTCTTTTA

CAGCTCGAGCCACTTCGTTTACCTGTTCCATCCGGCCCAATTCTTCCGG

CAGAAAGTCCCGCGTAAAAGCTACGCCTACTGCCAAGCGCTTTCCTGGC

TTAGCTGGTTCCTGGACATCTTTTCGGACAAAGACAGTAATGTGCGGCG

TCATAACACCCTCAGTACCGCCTGACATTATAAACGCAACTTTTTTTAC

AACTTCTTCGCGGCTTATTCCCAATTTTTCTGCTAGATACATTGCTAGA

GATTGGGTAGCAAAACCGCGAGTAAAATCGTTAACACAACCATTACCTT

CCGTCTTGCCCAGAATAGCTACAATTTCAGCCGGATTAATCTTCCCTGA

GTCAATCAAAGTAGCCAACCCGCTGATATCATCAGGTGAGGCTGTTGGG

ATACGAAAGACTTCAACTTTTTGCAT.

The present invention provides a composition for remediation of a liquid comprising the CAH as described above, along with polyethylene glycol (PEG) and/or KCl. In certain embodiments, the PEG is PEG4000. In certain embodiments, the PEG is present at a concentration of 50-500 mM. In certain embodiments, the composition comprises 50-500 mM KCl. In certain embodiments, the liquid is water.

The present invention provides a device for remediation of a liquid comprising a matrix and one or more structurally stable cyanuric acid hydrolases or a composition for remediation of a liquid as described above. In certain embodiments, the liquid is water. In certain embodiments, the device further comprises a casing or housing for the matrix. In certain embodiments, the matrix is water-insoluble. In certain embodiments, the water-insoluble matrix is granular and/or porous. In certain embodiments, the water-insoluble matrix is an organic matrix or an inorganic matrix. In certain embodiments, the matrix is an organic matrix and the organic matrix is plastic, nylon, activated carbon, cellulose, agarose, chitin, chitosan, collagen and/or polystyrene. In certain embodiments, the matrix is an inorganic matrix and the inorganic matrix is glass, zeolite, silica, alumina, titania, zirconia, calcium alginate and/or celite. In certain embodiments, the device further comprises a permeable layer. In certain embodiments, the enzyme is imbedded in or on the permeable layer. In certain embodiments, the device further comprises at least one casing, wherein water flowing through the at least one casing contacts the enzyme.

The present invention provides methods of remediating a liquid comprising contacting the liquid from a circulating reservoir with the enzyme, composition, or the device described herein above to reduce the concentration of cyanuric acid in the liquid. In certain embodiments, the enzyme is present in pellet form. In certain embodiments, the liquid is contacted with the device described hereinabove by passing the water over or through the device. In certain embodiments, the circulating liquid reservoir is a pool, a swimming pool, a spa, a hot tub, a whirlpool bath, a fountain or a waterslide. In certain embodiments, the concentration of cyanuric acid in the liquid subsequent to treatment is less than 100 ppm. In certain embodiments, the concentration of cyanuric acid in the liquid subsequent to treatment ranges from 70 ppm to 30 ppm. In certain embodiments, the enzyme is present at a concentration of at least 2.5 mg per one cubic meter of the liquid. In certain embodiments, the liquid flows through the device. In certain embodiments, the liquid treatment comprises reducing a concentration of cyanuric acid in the liquid. In certain embodiments, the liquid treatment is effected during a time period of 20 hours or less. In certain embodiments, the passing of the liquid through the device is effected at a flow rate of at least 10 cubic meters per hour. In certain embodiments, the liquid is water.

BRIEF DESCRIPTION OF DRAWINGS

FIG. 3. Substrate specificity of the cyanuric acid hydrolase from *M. thermoacetica* ATCC 39073. (A) Compounds that are substrates. (B) Compounds that are not substrates.

DETAILED DESCRIPTION OF THE INVENTION

Figure 1:
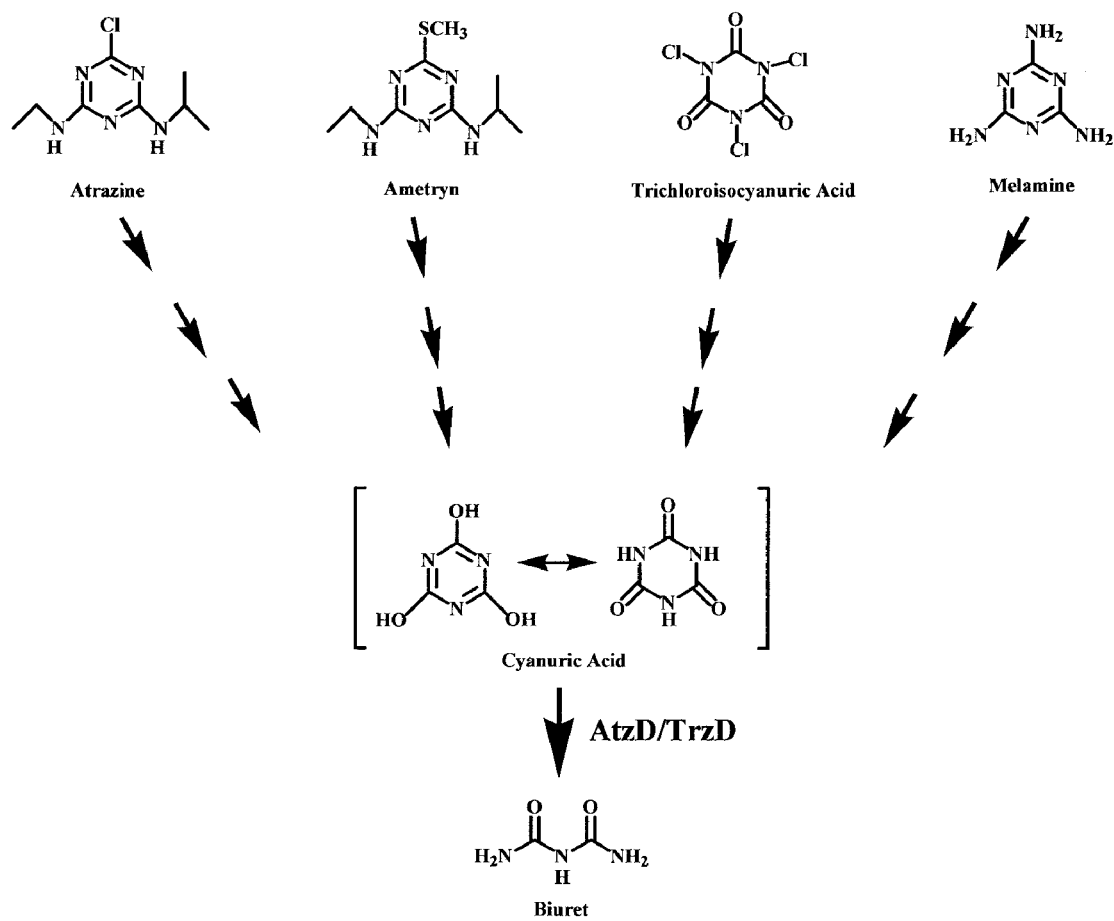
FIG. 1. Atrazine, ametryn, trichloroisocyanuric acid and melamine are all metabolized via cyanuric acid that is transformed to biuret by the action of cyanuric acid hydrolases.

Hypochlorous acid (HOCl) is a common source of free chlorine. Chemical compounds that release free chlorine are the most commonly used sanitizers in swimming pools. Hypochlorous acid, however, is highly unstable, and readily decomposes into inactive breakdown products, such as hydrochloric acid, water and oxygen, via UV radiation-driven photochemical reactions upon exposure to direct sun light, and/or upon exposure to moderate and high temperatures. On a typical summer day, up to 90% of the total active chlorine species are lost within two to three hours. In order to control these effects and preserve the effectiveness of the chlorine, the chlorine-stabilizing agent cyanuric acid (also called s-triazinetrione or isocyanuric acid) is often added to the water. Cyanuric acid, as well as cyanurate salts and various derivatives thereof are compounds which protect the chlorine from the negative effects of UV and heat, and therefore practically reduce the amount of chlorine which needs to be added to the water in order to maintain safe conditions of disinfection. The protection action of these compounds is achieved by the ability of free chlorine ($Cl^+$) to reversibly bind to the nitrogen atoms in the cyanuric acid ring. With a correct dosing, cyanuric acid can reduce the chlorine consumption. However, incorrect balance of cyanuric acid can create an over-protective effect and hence substantially decrease the effectiveness of chlorine as a disinfectant.

Excessive amounts of cyanuric acid drive the equilibrium towards the uptake of free chlorine. Hence, excessive amounts of cyanuric acid cause the chlorine to become progressively over-stabilized, reducing the availability of free chlorine and interfering with its disinfection function. The phenomenon, known as "chlorine-lock", takes place when the concentration of cyanuric acid reaches over 100 ppm (0.77 mM). Chlorine-lock expresses itself similarly to inadequately low chlorine level, in clouding of the pool's water which, apart from an aesthetic nuisance, is a clear indication that the water is no longer safe for use. Once added to the pool, cyanuric acid does not dissipate or degrade substantially. It is removed from the pool only by splash-out and backwash waste procedures or dilution. Typically, cyanuric acid level is lowered by draining part of the pool's water and diluting the remaining water with fresh water. If the cyanuric acid level exceeds 100 ppm considerably, the pool should be partially or totally drained and have its inner-walls scrubbed (cyanuric acid will sediment on the sides of the pool). This time-consuming and water-wasteful process is extremely costly not only in terms of water but also in loss of the pool's operational time, additional stabilized chlorine added, and the so far unavoidable reiterative nature of the overall process needed to maintain the balance between the concentration of reactive chlorine species and the concentration of cyanuric acid.

The present invention provides structurally stable cyanuric acid hydrolase enzymes, compositions and devices for removing excess cyanuric acid, e.g., from pool water, without the need to drain the water and/or diluting the remaining water.

Structurally Stable Cyanuric Acid Hydrolase Enzymes

A cyanuric acid hydrolase is an enzyme that specifically hydrolyzes cyanuric acid. As used herein "specifically hydrolyzes" means that less than 1% of the enzyme's activity is on other substrates besides cyanuric acid. As used herein, a "cyanuric acid hydrolase" is an enzyme that hydrolytically catalyzes the ring-opening reaction that converts cyanuric acid to biuret. Cyanuric acid hydrolase enzymes are well known in the art and have been isolated from various sources, some of which were characterized by their amino acid sequence, $K_M$ (Michaelis constant), Vmax, inhibitors thereof, and other biochemical parameters. The Michaelis constant represents the dissociation constant (affinity for substrate) of the enzyme-substrate complex. Low values indicate that this complex is held together very tightly and rarely dissociates without the substrate first reacting to form the product. In order that an enzyme would be used effectively for treating liquids (such as water) in large volumes and rate, the enzyme needs to be an efficient catalyst; hence the biometric parameters of cyanuric acid hydrolase are significant in the context of the present invention. The catalysis parameters of cyanuric acid hydrolase on cyanuric acid, namely $K_M$ values of 25-125 μM as presented herein, signify that these enzymes can be used effectively to reduce the concentration of cyanuric acid in the liquid, such as water, so as to achieve a concentration lower than the chlorine-lock concentration of 100 ppm (corresponding to 0.77 mM). Even at the highest allowable concentration of cyanuric acid in such water, 0.62 mM, the enzyme is highly effective and can produce the desired hydrolysis. The cyanuric acid hydrolase of the present invention has $k_{cat}$ values for cyanuric acid of 4.8-76 $s^{-1}$.

The present inventors discovered that the number of Lys residues is considerably higher in Moorella as compared to other enzymes with similar structure and function. AtzD had 7, TrzD had 12, but Moorella CAH had 21. Many of these are conservative changes, replacing the lower numbers of Arg's, but some are not. The inventors also looked at acidic and basic residues as a potential metric for salt bridges.

Arg+Lys=32 AtzD/36TrzD/41 Moorella (due mainly to the Lys as mentioned above)

Asp+Glu=43 atzd/50 trzd/50 Moorella

The global amino acid composition of these various proteins was also examined. The CAH from Bradyrhizobium USDA 110 was also compared as a control for random deviations. The relative stability for these proteins is as follows:

Bradyrhizobium CAH (loses activity in weeks)<AtzD (stable for months at 4° C., but loses activity by 9 months)<TrzD (kept activity for 9 mo., but cannot freeze without loss of activity)<Moorella The following values are expressed in % amino acids instead of absolute numbers of particular amino acids, as given above:

R+K=8.7 brady/8.8 atzd/9.7 trzd/11.1 Moorella

E+D=10.6 brady/11.9atzd/13.5trzd/13.7 Moorella

Sources of cyanuric acid hydrolases include man-made biological sources such as native and/or genetically modified microorganisms, plants and animals, which produce or overproduce the enzyme. The present inventors discovered a class of cyanuric acid hydrolases that are unusually stable at various temperatures. These enzymes are "structurally stable" in that they retain their catalytic activity at a broad temperature range, and can be stored for long periods of time under a wide range of conditions with minimal decrease in enzymatic activity. In certain embodiments, the cyanuric acid hydrolase retains at least 30% enzymatic activity at a temperature above 25° C. In certain embodiments, the cyanuric acid hydrolase is a thermostable enzyme. In general, thermostable enzymes also have a greater overall stability under a variety of conditions, such as to immobilization, to salt, to solvents, to low osmotic strength, etc. Thermostable enzymes hold their structural elements together more tightly, preventing the protein from irreversibly denaturing.

Many s-triazine compounds degrade to the metabolic intermediate cyanuric acid. Cyanuric acid can be further metabolized to biuret by cyanuric acid hydrolase. Cyanuric acid accumulates in swimming pools due the breakdown of the sanitizing agents di- and tri-chloroisocyanuric acid. The present inventors have discovered structurally stable cyanuric acid hydrolases that can be used in pool water remediation. In one embodiment, cyanuric acid hydrolase from the thermophile Moorella thermoacetica ATCC 39073 was cloned, expressed in Escherichia coli, and purified to homogeneity. The recombinant enzyme was found to have a broader temperature range and greater stability at both elevated and low temperatures, in comparison to previously described cyanuric acid hydrolases. The enzyme had a narrow substrate specificity acting only on cyanuric acid and N-methylisocyanuric acid. The *M. thermoacetica* enzyme did not require metals or other discernible cofactors for activity.

It was unexpected that the *M. thermoacetica* cyanuric acid amidohydrolase ATCC 39073 had enzymatic activity as a cyanuric acid hydrolase. In earlier studies, the *M. thermoacetica* cyanuric acid amidohydrolase from ATCC 39073 was indicated instead as a barbiturase. Support for it being a barbiturase was based on the fact that it has 48 percent amino acid-identity to barbiturase (48% ID). For example, a barbiturase from *Streptosporangium roseum* DSM 43021 is 43 and 46% identical to AtzD and TrzD, even though AtzD and TrzD are both cyanuric acid hydrolases. Thus, an enzyme's percent-identity with other known enzymes of a certain specificity does not guarantee that the enzyme of interest will also have the same substrate specificity (i.e., it is isofunctional). Merely observing the sequence of the putative gene in its genome context is not indicative of its function.

Cyanuric acid amidohydrolases share the following sequence consensus strings (where only one of the amino acids in parentheses is present in that position):

| Sequence | SEQ ID NO |
|---|---|
| (G/A)KTEGNG(C/G)VND(Y/F)(T/S)R | 5 |
| (V/I)MSGGTEG(V/A/G)(L/M)(S/A/T)PH | 6 |
| E(E/H/D/A)XG(R/T) | 7 |
| (D/Q)(L/V/A)H(F/Y/L)VQ(V/I)KCPLLT | 8 |
| SM(G/A/S)(Y/F/L)(S/N)R(G/A)A(S/A)ALG | 9 |
| (S/A/G)(A/T/C)S(S/A/G)G(I/V/G/S)ELX2(N/D/C/H)(V/E)X4G(M/N)(S/A)X2(S/A/W) | 10 |
| HX(V/E)MXD(A/G)(I/M)D | 11 |
| KAE | 12 |
| (R/D)(G/N)XR(H/N)(T/I)M(L/H/N)(S/T/D/E)D(S/T)D(I/V)(N/S/A)XTR(H/S)AR(A/G) | 13 |
| (V/I/L)(F/Y)VSGG(S/A/G)EHQGP(A/D/P)GGGP | 14 |

"Naturally occurring" is used to describe a substance or molecule that can be found in nature as distinct from being artificially produced. For example, a protein sequence present in an organism (including a virus), which can be isolated from a source in nature and which has not been intentionally modified in the laboratory, is naturally occurring.

A "variant" of an enzyme is a sequence that is substantially similar to the sequence of the native enzyme. "Wild-type" or "naturally occurring" or "native" refers to the normal gene, or organism found in nature without any known mutation. Variant amino acid sequences include synthetically derived amino acid sequences, or recombinantly derived amino acid sequences. Generally, amino acid sequence variants of the invention will have at least 40, 50, 60, to 70%, e.g., 71%, 72%, 73%, 74%, 75%, 76%, 77%, 78%, to 79%, generally at least 80%, e.g., 81-84%, at least 85%, e.g., 86%, 87%, 88%, 89%, 90%, 91%, 92%, 93%, 94%, 95%, 96%, 97%, to 98%, sequence identity to the native (endogenous) amino acid sequence.

The present invention includes variants of naturally-occurring cyanuric acid hydrolases. By "variant" an enzyme is intended as an enzyme derived from the native enzyme by deletion (so-called truncation) or addition of one or more amino acids to the N-terminal and/or C-terminal end of the native enzyme; deletion or addition of one or more amino acids at one or more sites in the native enzyme; or substitution of one or more amino acids at one or more sites in the native enzyme. The enzyme of the invention may be altered in various ways including amino acid substitutions, deletions, truncations, and insertions. Methods for such manipulations are generally known in the art. For example, amino acid sequence variants of the enzyme can be prepared by mutations in the DNA. Methods for mutagenesis and nucleotide sequence alterations are well known in the art. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall enzyme retains its spatial conformation but has altered biological activity. For example, common conserved changes might be Asp to Glu, Asn or Gln; His to Lys, Arg or Phe; Asn to Gln, Asp or Glu and Ser to Cys, Thr or Gly. Alanine is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "comparison window" makes reference to a contiguous and specified segment of an amino acid or polynucleotide sequence, wherein the sequence in the comparison window may comprise additions or deletions (i.e., gaps) compared to the reference sequence (which does not comprise additions or deletions) for optimal alignment of the two sequences. Generally, the comparison window is at least 20 contiguous amino acid residues or nucleotides in length, and optionally can be 30, 40, 50, 100, or longer.

As used herein, "percentage of sequence identity" means the value determined by comparing two optimally aligned sequences over a comparison window, wherein the portion of the polypeptide or polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70%, 71%, 72%, 73%, 74%, 75%, 76%, 77%, 78%, or 79%, at least 80%, 81%, 82%, 83%, 84%, 85%, 86%, 87%, 88%, or 89%, at least 90%, 91%, 92%, 93%, or 94%, and at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, or at least 95%.

The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to the reference sequence over a specified comparison window. An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

The term "amino acid" includes the residues of the natural amino acids (e.g., Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g., phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g., acetyl or benzyloxycarbonyl), as well as natural and unnatural amino acids protected at the carboxy terminus (e.g., as a $(C_1\text{-}C_6)$alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein).

The invention encompasses isolated or substantially purified protein compositions. In the context of the present invention, an "isolated" or "purified" polypeptide is a polypeptide that exists apart from its native environment and is therefore not a product of nature. The terms "polypeptide" and "protein" are used interchangeably herein. An isolated protein molecule may exist in a purified form or may exist in a non-native environment such as, for example, a transgenic host cell or bacteriophage. For example, an "isolated" or "purified" protein, or biologically active portion thereof, is substantially free of other cellular material, or culture medium when produced by recombinant techniques, or substantially free of chemical precursors or other chemicals when chemically synthesized. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed proteins or partial-length proteins encoded thereby are also encompassed by the present invention. By "fragment" or "portion" is meant a full length or less than full length of the amino acid sequence of a protein.

Thus, the genes and nucleotide sequences of the invention include both the naturally occurring sequences as well as mutant forms. Likewise, the polypeptides of the invention encompass naturally occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations."

By "portion" or "fragment," as it relates to a nucleic acid molecule, sequence or segment of the invention, when it is linked to other sequences for expression, is meant a sequence having at least 80 nucleotides, more preferably at least 150 nucleotides, and still more preferably at least 400 nucleotides.

If not employed for expressing, a "portion" or "fragment" means at least 9, preferably 12, more preferably 15, even more preferably at least 20, consecutive nucleotides, e.g., probes and primers (oligonucleotides), corresponding to the nucleotide sequence of the nucleic acid molecules of the invention.

Nucleic Acids Encoding Structurally Stable Cyanuric Acid Hydrolases

The present invention includes isolated nucleic acids and vectors that encode the structurally stable cyanuric acid hydrolases described above.

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues. A "nucleic acid fragment" is a fraction of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA that can be single- or double-stranded, optionally containing synthetic, non-natural or altered nucleotide bases capable of incorporation into DNA or RNA polymers. The terms "nucleic acid," "nucleic acid molecule," "nucleic acid fragment," "nucleic acid sequence or segment," or "polynucleotide" may also be used interchangeably with gene, cDNA, DNA and RNA encoded by a gene.

The invention encompasses isolated or substantially purified nucleic acid compositions. In the context of the present invention, an "isolated" or "purified" DNA molecule or an "isolated" or "purified" polypeptide is a DNA molecule that exists apart from its native environment and is therefore not a product of nature. An isolated DNA molecule may exist in a purified form or may exist in a non-native environment such as, for example, a transgenic host cell or bacteriophage. For example, an "isolated" or "purified" nucleic acid molecule, or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Fragments and variants of the disclosed nucleotide sequences encoded thereby are also encompassed by the present invention. By "fragment" or "portion" is meant a full length or less than full length of the nucleotide sequence encoding the amino acid sequence of a protein.

The term "gene" is used broadly to refer to any segment of nucleic acid associated with a biological function. Thus, genes include coding sequences and/or the regulatory sequences required for their expression. For example, gene refers to a nucleic acid fragment that expresses mRNA, functional RNA, or specific protein, including regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

A "vector" is defined to include, inter alia, any plasmid, cosmid, phage or binary vector in double or single stranded linear or circular form which may or may not be self transmissible or mobilizable, and which can transform prokaryotic or eukaryotic host either by integration into the cellular genome or exist extrachromosomally (e.g., autonomous replicating plasmid with an origin of replication).

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

Such expression cassettes will comprise the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

"Operably-linked" refers to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

Compositions for Remediation of Liquid

Certain embodiments of the present invention provide compositions for use in the remediation of a liquid, such as water, for example swimming pool water. The compositions include one or more structurally stable cyanuric acid hydrolases described above. In certain embodiments, the composition further comprises polyethylene glycol and/or KCl. The compositions can be used for treating a liquid in order to maintain a chemical balance in the liquid by reducing the level of cyanuric acid in the liquid.

Devices for Remediation of Liquid

Certain embodiments of the present invention provide devices for use in the remediation of a liquid, such as water, for example swimming pool water. The devices include a matrix and one or more structurally stable cyanuric acid hydrolases described above, where the enzymes are incorporated in, into, or on the matrix. In certain embodiments, the enzymes are incorporated in or on a water-insoluble matrix, which serves as a solid support for the enzyme, namely, it provides a stationary object with respect to the water and the various chemicals dissolved in it. The water-insoluble matrix allows performing a continuous and/or repetitive contact of the treated water with the enzyme, as well as maintaining the enzyme affixed, thus eliminating loss of the enzyme due to leaching out.

Many commercially available solid-phase synthesis columns, purification and ion-exchange columns are packed with granular and/or porous water-insoluble and water-permeable matrices that are suitable for protein immobilization applications, or can readily be modified so as to be suitable for protein immobilization, and therefore are suitable for use as the water-insoluble matrix according to the present invention. Such granular and/or porous water-insoluble matrices are well known in the art and are used in various applications such as filtration and chromatography. Representative examples include, without limitation, organic substances such as nylons, polystyrenes, polyurethanes and other synthetic polymers and co-polymers, activated carbon, cellulose, agarose, chitin, chitosan and collagen, and inorganic substances such as beads, filters, cloth, glass, plastic, zeolite, silica, alumina, titania, zirconia, calcium alginate and celite.

Other forms of organic polymers, copolymers and cross-linked derivatives thereof, and inorganic materials such as diatomaceous earths and other types of molecular sieves, typically used in various water filtrations, can be used as a granular and/or porous water-insoluble matrix, according to the present invention, on or in which an enzyme can be incorporated.

The term "incorporated," as used herein, refers to any mode of contact between the water-insoluble matrix and the enzyme which achieves immobilization of the enzyme with respect to the matrix, thus rendering a biochemically active enzyme insoluble, or in other words immobilized, and in some cases more protected, than the soluble enzyme.

Incorporation of an enzyme into or on the matrix can be effected by attachment via any type of chemical bonding, including covalent bonds, ionic (electrostatic) bonds, hydrogen bonding, hydrophobic interactions, metal-mediated complexation, affinity-pair bonding and the like, and/or by attachment via any type of physical interaction such as magnetic interaction, surface adsorption, encapsulation, entrapment, entanglement and the like. The enzyme(s) can be incorporated in and/or on physical structural elements of a water-insoluble matrix. In cases where the structural elements of the matrix are granular but not porous, such as, for example, in cases where the matrix is made of solid glass beads or particles, or solid plastic beads or particles, the enzyme(s) is incorporated on the surface of the beads or particles, and the water that flows in the channels between the beads or particles comes in contact with the enzyme(s), thus allowing the amide-containing compounds dissolved in the water to be enzymatically degraded.

In cases where the structural element of the matrix is porous but not granular, such as, for example, in cases where the matrix is extruded zeolite blocks, carbonaceous blocks or solid plastic foam blocks, the enzyme(s) is incorporated in the cavities, on the inner surface of the innate inter-connected pores and channels which are characteristic to such matrices, as well as on the outer surface of the block, and the water that flows in the inter-connected pores and channels comes in contact with the enzyme(s). In cases where the structural elements of the matrix are granular and porous, such as, for example, in cases where the matrix is zeolite granules or molecular sieves pellets, the enzyme(s) is incorporated on the surface of the granules or pellets and in the inner surface of the pores and channels of these matrices, and the water that flows between the granules or pellets as well as through them comes in contact with the enzyme(s), thus allowing the amide-containing compounds dissolved in the water to be enzymatically degraded.

In certain embodiments, the incorporation of the enzyme to the water-insoluble matrix is effected by a combination of chemical and physical attachments such as covalent bonding and entanglement.

In certain embodiments of the present invention, the incorporation of the enzyme to the water-insoluble matrix is effected by covalently attaching the enzyme to the water-insoluble matrix (the solid support) by conventional methods known in the art for enzyme immobilization.

Exemplary immobilization techniques are described for example in U.S. Pat. Nos. 4,071,409, 4,090,919, 4,258,133, 4,888,285, 5,177,013, 5,310,469, 5,998,183, 6,905,733, and 6,987,079, U.S. Patent Application Publication No. 2003/0096383, and in Yan-A-X. et al, 2002, Applied Biochemistry and Biotechnology, Vol. 101(2), pp. 113-130(18); and Ye, Yun-hua et al, 2004, Peptide Science, Vol. 41, pp 613-616, which are incorporated herein by reference. Briefly, protein immobilization by covalent bonding to a solid matrix, according to certain embodiments of the present invention, is based on coupling two functional groups, as these are defined hereinbelow, one within the matrix (e.g., on its surface) and the other within the enzyme (e.g., on its surface), either directly or via a spacer. The spacer can be, for example, a bifunctional moiety, namely, a compound having at least two functional groups which are capable of forming covalent bonds with functional groups of both the matrix and the enzyme. As used herein, the phrase "functional group" describes a chemical group that has certain functionality and therefore can participate in chemical reactions with other components which lead to chemical interactions as described hereinabove (e.g., a bond formation). The phrase "cross-linking agent," as used herein, refers to a bifunctional compound that can promote or regulate intermolecular interactions between polymer chains, linking them together to create a more rigid structure. Cross-links are bonds linking functional groups of polymers and/or other substances, so as to form intermolecular interactions therebetween and, as a result, a three-dimensional network interconnecting these substances. Cross-linking can be effected via covalent bonds, metal complexation, hydrogen bonding, ionic bonds and the like.

Water-treatment devices that are suitable for use in the context of the present invention are described, for example, in U.S. Pat. Nos. 4,532,040, 4,935,116, 5,055,183, 5,478,467, 5,855,777, 5,980,761, 6,257,242 and 6,325,929, which are incorporated by reference.

Water treatment devices utilized in circulating reservoirs typically form a part of a larger system, which is typically referred to as a water plant. Typical water treatment devices used in water plants of circulating reservoirs exert their designated treatment action when water flows therethrough, either by means of a pump or by gravity. The water flows into the system, enters the device, and passes through a water-permeable and water-insoluble matrix within the device, which effects the designated treatment action, typically filtration of insoluble particulates and objects, chemical exchange of solutes and ions and dissolution and addition of chemicals into the water.

The device containing the composition described herein can therefore be any device, or part of a device through which water flows during the process of treating the water. Such a device can be, for example, one or more of a filter, a filter cartridge, an ion-exchanger, an erosion feeder and the likes, as is exemplified hereinbelow. The device may be a removable device such as a removable filter cartridge. Such a removable device can be manufactured and sold separately as a "replacement" cartridge.

Thus, according to certain embodiments, the composition of the present invention can be added to a water-treatment device having a water-treatment substance embedded therein which effects the originally designated treatment action of these devices, or replace that substance altogether.

The device, according to the present embodiments, can form a part of a comprehensive water treatment system, which exerts other water treatment actions, such as filtration of solid particulates and addition of chemicals. Water that flows through such a water-treatment system also flows through the device presented herein. The system can be design such that all its water capacity flows through the device, or such that only a part of its water capacity flows therethrough.

Typically, the flow rate can be adjusted per device for the optimal function of the system and every device in it. For an efficient function of the present device, which includes an immobilized active enzyme, the amount of enzyme, amount of water-insoluble matrix, overall shape of the device and flow-rate need to be designed to as to suit the system's layout, water capacity (power) and the expected rate at which the concentration of an amide-containing compound such as, for example, cyanuric acid, is required to be reduced. The rate of an amide-containing compound reduction depends on the enzymatically catalyzed reaction condition, e.g., temperature, pH, ionic strength and, in relevance to this case, water flow. All the abovementioned parameters are considered while designing the device.

The incorporation of enzymes to water-insoluble matrices is typically measured in international units of activity. An international unit (IU) of an enzyme is defined as the amount of enzyme that produces one micromole of a reaction product in one minute under defined reaction conditions. The amount of IU which can be incorporated to a matrix depends on the type of matrix and incorporation technique, surface area of the matrix, the availability and chemical reactivity of functional groups suitable for conjugation in both the enzyme and the matrix, and on the residual enzymatic activity subsequent to the incorporation process. Typical enzyme load ranges from a few IU to hundreds of IU of an enzyme per $cm^3$ of matrix material. An optimal load, namely, the optimal amount of enzyme to be incorporated per a unit volume of water-insoluble matrix material, is an example of one parameter that is considered while designing the device.

The water-treatment device presented herein is shaped and sized, and its through-flow is designed, so as to achieve optimized efficacy in reducing the concentration of the desired amide-containing compound (e.g., cyanuric acid). For example, using the enzymatic catalysis parameters presented hereinabove for structurally stable cyanuric acid hydrolase, one can calculate that for a water quantum of 100 cubic meters, 250 mg of cyanuric acid hydrolase is capable of treating this water quantum by decreasing the cyanuric acid concentration from 100 ppm to 50 ppm within a time period of 20 hours. Considering typical water pumps used in water treatment systems of pools, which can transfer an average of 11 cubic meters per hour, this water quantum will be treated by 250 mg of cyanuric acid amidohydrolase once in 9.09 hours and more than twice in 20 hours, which is an acceptable rate of cyanuric acid degradation.

A reduction of 50 ppm in cyanuric acid concentration translates to approximately 50 grams of cyanyric acid (about 0.4 moles) per cubic meter of water at chlorine-lock conditions. Therefore, about 280 IU of cyanuric acid amidohydrolase are required in order to reduce the concentration of cyanuric acid in one cubic meter of water within a time period of 24 hours.

As used herein, the term "about" means ±10%.

Thus, according to certain embodiments of the present invention the amount of cyanuric acid hydrolase required to treat one cubic meter of water within a time period of 24 hours ranges from 0.5 mg to 10 mg per, preferably 1 to 5, and more preferably the amount of cyanuric acid amidohydrolase is at least 2.5 mg per one cubic meter of treated water.

As mentioned hereinabove, in the water-treatment device described herein, the composition presented herein is embedded in a casing.

The casing may be used so as to avoid sweeping of the composition-of-matter by the water passing through the device. Another purpose of a casing is to form the desired shape and cross-section of the device, which will optimize its function and maintain a continuous, void-free bed of the composition-of-matter presented herein. The casing material is preferably selected suitable for water high-pressure, and is typically water-insoluble and water-tight. Furthermore, the casing material is preferably selected inactive and stable with respect to water and the chemicals that are typically found in circulating reservoirs. Examples for suitable casing materials include, without limitation, plastic, galvanized metal and glass. In preferred embodiments, the device for water treatment of the present invention includes a casing with two parallel perforated faces, constituting a semi-closed compartment, whereby the composition presented herein fills, or partially fills the compartment. The casing thus has one perforated face for a water inlet, and the other perforated face for a water outlet. The water to be treated (containing the amide-containing compound(s)) enters the inlet, pass through the compartment containing the composition, and come in contact with the permeable and water-insoluble matrix having the enzyme(s) incorporated therein or thereon.

In certain embodiments, the device may include an immobilizing matrix that has a permeable layer. Such an enzyme-containing matrix could serve as a stationary phase for the reservoir's water.

Other exemplary devices for water treatment according to certain embodiments of the present invention may be a filter cartridge, similar to that disclosed, for example, in U.S. Pat. No. 6,325,929, and containing, as the composition, an extruded solid, water-permeable carbonaceous material block as a water-insoluble matrix and one or more amidohydrolase enzyme(s) incorporated in and on the carbonaceous block.

Methods of Remediating Water

Certain embodiments of the present invention provide devices for use in the remediation of water, such as swimming pool water. In certain embodiments, the method involves the treatment of water with the enzymes, compositions or devices described above. In certain embodiments, in order for the treatment to be effective, it is desirable that the water flow at a certain rate so as to come in contact with an effective amount of the hydrolase for a certain period of time.

In certain embodiments, the method involves adding the CAH enzyme to a liquid, such as water, in the form of a free enzyme, or can be present as part of a device or part of a device through which water flows through or over during the process of treating the water.

In certain embodiments of the invention, the water treatment is effected by reducing a concentration of cyanuric acid in the water. In methods of the present invention, the water is contacted with the device described hereinabove, such as by passing the water through the device.

The phrase "circulating reservoir," as used herein, refers to a structure for holding a relatively large amount of water. The relatively large amount of water means that the water is not replaced after every use, or rarely replaced in general for a long period of time in terms of months and hence maintaining the water is typically achieved by a circulating procedure. In order to maintain the water, it at least partially pumped or otherwise transferred out of the structure and then back into the reservoir by means of a water transferring device such as, for example, a pump, while being passed via a water treatment plant. Typical, presently used, water treatment plants include water treatment devices, such as, for example, sensors, detectors, heaters, coolers, chemical feeders, chemical exchangers and filters of various purposes and designs.

In certain embodiments the circulating reservoirs are public and/or private reservoirs that are used by humans for hygiene, sports, professional training, recreation, amusement, therapeutic and general bathing and for ceremonial and aesthetic purposes, and include, without limitation, pools, artificial ponds and lakes, swimming pools, spas, hot tubs, whirlpool baths, fountains and waterslides. The water treatment system that houses the device and effect water flow through the device by means of, for example, water pumps, distribution manifolds, hoses and pipes, spigots and valves.

As discussed above, chlorine-lock occurs when the concentration of cyanuric acid reaches 100 ppm, rendering the quality of the water in the circulating reservoir unacceptable. In general, water needed to be treated is generally at 50-200 ppm, and the goal is to get it below 30 ppm. Thus, in certain embodiments, the method acts to reduce the concentration of cyanuric acid in the water, subsequent to the treatment, to less than 100 ppm. In certain embodiments, the concentration of cyanuric acid in the water, subsequent to the treatment, ranges from 70 ppm to 30 ppm.

In certain embodiments, the amount of the structurally stabile cyanuric acid hydrolase is at least 2.5 mg per one cubic meter of the water.

In addition to treating the water of circulating reservoirs in order to reach the desired concentration of cyanuric acid in the water, in certain embodiments the desired effect of water treatment would be achieved within a relatively short period of time. The time period should be minimized so as to avoid loss of operational time of circulating reservoir, and avoid the risk of reaching chlorine-lock due to the continuous addition of stabilized sanitizers. The length of the time period within which the treatment takes place depends on the amount of water to be treated, the capacity of the water-treatment system and the amount and the catalytic efficiency of the enzyme, as discussed hereinabove.

To demonstrate an exemplary implementation of the method of treating water according to the present invention, one can consider an exemplary circulating reservoir such as an Olympic swimming pool. An Olympic swimming pool that meets international standards as defined by The International Swimming Federation, must be 50 meters in length by 25 meters wide by at least 2 meters in depth. Among other standards, the water must be kept at 25-28° C. and the lighting level at greater than 1500 lux. There are thus at least 2500 cubic meters of water (660,430 U.S. liquid gallons) which must be treated in a standard Olympic pool.

Using the calculation for the sufficient amount of cyanuric acid hydrolase needed to treat 100 cubic-meters of water, i.e., to reduce the cyanuric acid concentration from 100 ppm to 50 ppm within about 20 hours, as presented hereinabove, the water of an Olympic pool in a state of chlorine-lock should be passed twice through one or more devices, as presented herein, and be brought in contact with a composition-of-matter comprising cyanuric acid hydrolase, according to the present invention. The molecular weight of cyanuric acid is 129.07, so 50 ppm of a 100,000 L pool has 38.7 moles of cyanuric acid. Assuming the enzyme had 10 µmol/min/mg specific activity and contact time was 1200 minutes, then 3.2 g of enzyme would be required. This assumes that the enzyme had infinite number of turnovers and that it retained its original specific activity. This would be static contact time. With water flowing through the filter, the contact time would really be less than this. Basically, it would be 3870 divided by the number of minutes the water was in contact with the enzyme, in order to give the number of grams of enzyme needed. If one assumes that the water is pumped through the filter two times, then 1935 divided by the number of minutes the water was in contact with the filter on each pass would give the number of grams of enzyme needed. For hypothetical sake, if one had a filter with a 5 minute contact time on each pass, then for two passes, one would need 397 grams of enzyme with a specific activity of 10 µmol/min/mg. If it was a one minute contact time then for the same two passes, one would need 1935 grams of enzyme.

GENERAL TERMINOLOGY

"Synthetic" nucleic acids are those prepared by chemical synthesis. The nucleic acids may also be produced by recombinant nucleic acid methods. "Recombinant nucleic acid molecule" is a combination of nucleic acid sequences that are joined together using recombinant nucleic acid technology and procedures used to join together nucleic acid sequences as described, for example, in Sambrook and Russell (2001).

As used herein, the term "nucleic acid" and "polynucleotide" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues.

A "nucleic acid fragment" is a portion of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" may also be used interchangeably with gene, cDNA, DNA and RNA encoded by a gene, e.g., genomic DNA, and even synthetic DNA sequences. The term also includes sequences that include any of the known base analogs of DNA and RNA.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have in at least one embodiment 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

The term "gene" is used broadly to refer to any segment of nucleic acid associated with a biological function. Genes include coding sequences and/or the regulatory sequences required for their expression. For example, gene refers to a nucleic acid fragment that expresses mRNA, functional RNA, or a specific protein, including its regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters. In addition, a "gene" or a "recombinant gene" refers to a nucleic acid molecule comprising an open reading frame and including at least one exon and (optionally) an intron sequence. The term "intron" refers to a DNA sequence present in a given gene which is not translated into protein and is generally found between exons.

"Naturally occurring," "native" or "wild type" is used to describe an object that can be found in nature as distinct from being artificially produced. For example, a nucleotide sequence present in an organism (including a virus), which can be isolated from a source in nature and which has not been intentionally modified in the laboratory, is naturally occurring. Furthermore, "wild-type" refers to the normal gene, or organism found in nature without any known mutation.

"Homology" refers to the percent identity between two polynucleotides or two polypeptide sequences. Two DNA or polypeptide sequences are "homologous" to each other when the sequences exhibit at least about 75% to 85% (including 75%, 76%, 77%, 78%, 79%, 80%, 81%, 82%, 83%, 84%, and 85%), at least about 90%, or at least about 95% to 99% (including 95%, 96%, 97%, 98%, 99%) contiguous sequence identity over a defined length of the sequences.

"Operably-linked" nucleic acids refers to the association of nucleic acid sequences on single nucleic acid fragment so that the function of one is affected by the other, e.g., an arrangement of elements wherein the components so described are configured so as to perform their usual function. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. Control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

As discussed above, the terms "isolated and/or purified" refer to in vitro isolation of a nucleic acid, e.g., a DNA or RNA molecule from its natural cellular environment, and from association with other components of the cell, such as nucleic acid or polypeptide, so that it can be sequenced, replicated, and/or expressed. For example, "isolated nucleic acid" may be a DNA molecule that is complementary or hybridizes to a sequence in a gene of interest and remains stably bound under stringent conditions (as defined by methods well known in the art). Thus, the RNA or DNA is "isolated" in that it is free from at least one contaminating nucleic acid with which it is normally associated in the natural source of the RNA or DNA and in one embodiment of the invention is substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

As used herein, the term "recombinant nucleic acid," e.g., "recombinant DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome that has not been transformed with exogenous DNA. An example of preselected DNA "derived" from a source would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. Therefore, "recombinant DNA" includes completely synthetic DNA sequences, semi-synthetic DNA sequences, DNA sequences isolated from biological sources, and DNA sequences derived from RNA, as well as mixtures thereof.

Nucleic acid molecules having base substitutions (i.e., variants) are prepared by a variety of methods known in the art. These methods include, but are not limited to, isolation from a natural source (in the case of naturally occurring sequence variants) or preparation by oligonucleotide-mediated (or site-directed) mutagenesis, PCR mutagenesis, and cassette mutagenesis of an earlier prepared variant or a non-variant version of the nucleic acid molecule.

The invention will now be illustrated by the following non-limiting Examples.

EXAMPLE 1

Thermostable Cyanuric Acid Hydrolase

Microbial enzymatic degradation of cyanuric acid has been studied previously (Devers, M., et al., 2007. *FEMS Microbiol Lett.* 273:78-86; Eaton, R. W., and J. S. Karns. 1991. *J. Bacteriol.* 173:1363-1366; Fruchey, I., N. et al., 2003. *Appl Environ Microbiol.* 69:3653-7; Smith, D., S. Alvey, and D. E. Crowley. 2005. *FEMS Microbiol Ecol.* 53:265-73). Two distinct but homologous enzymes, AtzD from *Pseudomonas* sp. strain ADP (Fruchey, I., N. et al., 2003. *Appl Environ Microbiol.* 69:3653-7) and TrzD from *Pseudomonas* sp. strain NRRLB-12227 (Smith, D., S. Alvey, and D. E. Crowley. 2005. *FEMS Microbiol Ecol.* 53:265-73), have been studied in detail. These enzymes, known as cyanuric acid hydrolases, catalyze the conversion of cyanuric acid to biuret (FIG. 1). Biuret is not considered toxic to humans and degrades more readily than cyanuric acid.

Barbiturase is the only protein known to be homologous to cyanuric acid hydrolase that has a defined and different physiological function. Barbiturase catalyzes the conversion of barbituric acid to ureidomalonic acid in organisms that catabolize pyrimidines by the oxidative pathway. Barbiturase is unstable at 4° C. in the absence of ethylene glycol and dithiothrietol (DTT). Furthermore, activity is completely lost when the protein is maintained at 55° C. for 30 minutes (Soong, C. L., et al., 2002. *J Biol Chem.* 277:7051-8). AtzD and TrzD are relatively stable at 4° C., but they lose activity when frozen. Moreover, the thermostability properties of AtzD and TrzD are not well studied, but these enzymes are derived from mesophilic bacteria. In this context, the inventors initiated a search to identify a stable cyanuric acid hydrolase. Enzymes that are more stable to temperature changes are more stable to many environmental factors. Thus, a thermostable enzyme would be most applicable to pool water and other remediation efforts.

The inventors identified a cyanuric acid hydrolase homolog in *Moorella thermoacetica* ATCC 39073, an anaerobic, acetogenic bacterium that is able to grow at 65° C. The gene was cloned into *E. coli*, the protein was expressed at high levels, the recombinant *E. coli* degraded cyanuric acid, and the enzyme was obtained in homogeneous form by a convenient one-step purification. The enzyme's function as a cyanuric acid hydrolase was confirmed, and it was shown to be significantly more stable than other known members of the cyanuric acid protein family.

Materials and Methods

Chemicals. 5-nitrobarbituric acid, 5-methylbarbituric acid, 2-methylamino-4,6-dihydroxy-s-triazine, 1,3,5-trimethoxy-s-triazine, methyl isocyanurate, 2-(3-methoxypropylamino)-4,6-dihydroxy-s-triazine, triphenoxy-s-triazine, 2-secbutyl-4,6-dihydroxy-s-triazine, N-phenyl ammelide, 2-ethylamino-4,6-dihydroxy-s-triazine, triisopropoxy-s-triazine, trimethyl isocyanurate, and 1,3-dimethyl isocyanurate were prepared as previously described (Smolin, E. M., and L.

Rapoport. 1959. s-Triazines and Derivatives, p. 269-308. In A. Weissberger (ed.), The chemistry of heterocyclic compounds. Interscience Publishers Inc., New York). Hexazinone, 4,6-dihydroxy-2-mecapto pyrimidine and 4,6-dihydroxy-5-nitro-pyrimidine were purchased from Sigma-Aldrich.

Bacterial strains and growth conditions. *M. thermoacetica* ATCC 39073, formerly known as *Clostridium thermoacticum*, was obtained from the ATCC and grown anaerobically at 55° C. in serum bottles (125 ml) or in rubber-stoppered, screw-capped infusion flasks (1200 ml; Muller-Krempel, Bulach, Switzerland. The bacterium was grown in an anaerobic medium containing the following per liter: 5 g yeast extract, 5 g tryptone, 6.4 g $Na_2HPO_4$, 6.1 g $NaH_2PO_4$, 0.4 g $NH_4Cl$, 0.3 g $MgCl_2.6H_2O$, 0.05 g $CaCl_2.2H_2O$, 0.04 g $Fe(NH_4)(SO4)_2.6H_2O$, and 10 ml of a mineral mix which was previously described (Marsili, E., et al., 2008. *Appl. Environ Microbiol.* 74:7329-37). After autoclaving, 18 g glucose and 0.2 mg of biotin, cyanocobalamin, flavin mononucleotide, folic acid, nicotinic acid, p-aminobenzoic acid and thiamine pyrophosphate were added individually. Immediately before inoculation, 10 ml of a reducing solution, containing 0.36 g of $Na_2S.9H_2O$ and 0.36 g of cysteine HCl, were added. The pH of all media was adjusted to 6.6 prior to the addition of 2 g/l NaHCO3. The media was flushed with oxygen-free $N_2$—$CO_2$ (80:20 [vol/vol]) for 30 min prior to sealing with butyl rubber stoppers.

Protein identification and comparisons. The BLAST algorithm was used to identify homologs of AtzD, TrzD, and barbiturase. Sequence alignments were done with Clustal W (Thompson, J. D., D. G. Higgins, and T. J. Gibson. 1994. *Nucleic Acids Res.* 22:4673-4680.), and protein trees were constructed with the maximum likelihood algorithm in PHYLIP (Felsenstein, J. 1989. *Cladistics* 5:164-166). The protein sequences (GenBank accession numbers) used are as follows: *Pseudomonas* sp. strain ADP AtzD (AAK50331), *Pseudomonas* sp. strain NRRLB-12227 (now called *Acidovorax avenae* subsp. *citrulli*) TrzD (AAC61577), *Rhodococcus erythropolis* barbiturase (CAC86669), *Chelatobacter heintzii* (AAK52819), *Moorella thermoacetica* ATCC 39073 (YP_430955), *Bradyrhizobium japonicum* USDA 110 (BAC52546), and *Arthrobacter* sp. strain AD25 (ABK41866).

Cloning and expression. Total genomic DNA was extracted from cell pellets of *M. thermoacetica* ATCC 39073, *Pseudomonas* sp. strain NRRLB-12227 and *Pseudomonas* sp. strain ADP, as previously described (Sambrook, J., E. F. Fritsch, and T. Maniatis. 1989. Molecular Cloning: A Laboratory Manual, 2nd ed. Cold Spring Harbor Press, Cold Spring Harbor, N.Y; van der Maarel, et al., 1996. *Appl Environ Microbiol.* 62:3978-84). ORF Moth_2120 from *M. thermoacetica* ATCC 39073 was PCR amplified, using primers 5'-GCGAATTCCATATGCAAAAAGTTGAAGTCTT-3' (SEQ ID NO:1) and 5'-GCC AAGCTTCTACACCCTGGCAATAACAG-3' (SEQ ID NO:2) (NdeI and HindIII restriction enzyme sites underlined, respectively). The gene was cloned into a pET28b+ vector (Novagene, Madison, Wis.). The resulting vector, pET28b+:: Moth_2120, was transformed into *E. coli* BRL21(DE3) pLysS, and grown at 37° C. in Luria-Bertani medium (Sambrook, J., E. F. Fritsch, and T. Maniatis. 1989. Molecular Cloning: A Laboratory Manual, 2nd ed. Cold Spring Harbor Press, Cold Spring Harbor, N.Y.) containing 50 µg kanamycin and 25 µg chloramphenicol per ml. When the culture reached an optical density at 600 nm of 0.5, 1 mM isopropyl-D-thiogalactopyranoside (IPTG) was added, and the induced cells were grown overnight at 30° C. A similar cloning, expression, and purification system was used to clone and His-tag the trzD gene from *P.* sp strain NRRLB-12227 and atzD from *P.* sp strain ADP to obtain these enzymes for comparison.

Enzyme purification. For enzyme purification, 2 L of *E. coli* BRL21(DE3) (pET28b+::Moth 2120) cells were grown, as described above. The culture was centrifuged at 10,000×g for 20 mM at 4° C., and the pellet was resuspended (1 ml per gram cell) in 100 mM potassium phosphate buffer, pH 7.0. The cell suspension was passed three times through a chilled Amicon French pressure cell, operated at 140 MPa, and the crude cell lysate was centrifuged at 18,000×g for 90 min at 4° C. The enzyme was purified using a 5 ml HiTrap chelating HP column (Amersham Pharmacia Biotech AB, Uppsala, Sweden) and a Pharmacia FPLC LKB system (Amersham Pharmacia Biotech AB, Uppsala, Sweden). The column was prepared as per manufacturers instructions and equilibrated with 60 ml of 100 mM potassium phosphate buffer, pH 7.0. After loading the protein, the column was washed with a series of step gradients consisting of 0.05 M, 0.1 M, 0.25 M, and 0.5 M imidazole in 100 mM potassium phosphate buffer (pH 7.0). Purified protein was analyzed by sodium dodecyl sulfate-polyacrylamide gel electrophoresis (SDS-PAGE) for purity and subunit molecular weight determination by comparison to broad range standards (Bio-Rad Laboratories, Hercules, Calif.). The purified protein was dialyzed at 4° C. against 100 mM potassium phosphate buffer (pH 7.0) to remove imidazole.

Enzyme assay and kinetic constant determinations. Enzyme activity was monitored on a Beckman DU 640 spectrophotometer (Beckman Coulter, Fullerton, Calif.). Cyanuric acid and barbituric acid concentrations were measured at 214 nm (extinction coefficient=9200 $cm^{-1}M^{-1}$) and 256 nm, respectively. Reactions were carried out in 0.5 ml 25 mM Tris-HCl buffer, pH 8.0 with 100 µM cyanuric acid or barbituric acid at 30° C. Reactions were initiated by the addition of the enzyme. Kinetic parameters were determined by obtaining rates at cyanuric acid concentrations ranging from 10 to 110 µM. The data was plotted using Lineweaver-Burke plots.

Conversion of cyanuric acid to biuret was confirmed using high-pressure liquid chromatography (HPLC). Control samples, standards, and enzymatic reactions were set up in 5 mM phosphate buffer (pH 7.0). Samples were analyzed by HPLC, using a Hewlett-Packard HP 1100 system equipped with a photodiode array detector interfaced to an HP Chemstation. A mixed-mode $C_8$/anion 7µ column (250 by 4.6 mm) (Alltech, Deerfield, Ill.) was used with an isocratic mobile phase consisting of 95% methanol and 5% 5 mM phosphate buffer (pH 7.0).

Substrate specificity analysis. Seventeen compounds structurally analogous to cyanuric acid were tested as substrates: 5-nitrobarbituric acid, 5-methylbarbituric acid, 2-methylamino-4,6dihydroxy-s-triazine, 1,3,5-trimethoxy-s-triazine, 2-(3-methoxy propylamino)-4,6-dihydroxy-s-triazine, triphenoxy-s-triazine, 2-secbutyl-4,6-dihydroxy-s-triazine, N-phenyl ammelide, 2-ethylamino-4,6-dihydroxy-s-triazine, triisopropoxy-s-triazine, trimethyl isocyanurate, 1,3-dimethyl isocyanurate, hexazinone, 4,6-dihydroxy-2-mecapto pyrimidine, 4,6-dihydroxy-5-nitro-pyrimidine, barbituric acid and methyl isocyanurate. The compounds (100 µM) were incubated with 50 µg of purified enzyme in 25 mM Tris-HCl buffer (pH 8.0) for 30 min. Changes in the UV spectra were recorded. In cases where changes in the spectra were detected, an appropriate wavelength with absorbance differences between the substrate and product was chosen for further kinetic study. For N-methylisocyanurate, absorbance was measured at 214 nm (extinction coefficient=9500 cm$^{-1}$M$^{-1}$).

Effect of pH and temperature on enzymatic activity. The optimum pH of the enzyme was determined at 30° C. with the following buffers: 25 mM NaHCO$_3$/Na$_2$CO$_3$, pH 5-7; 25 mM Tris-HCl, pH 7-9; NaHCO$_3$/Na$_2$CO$_3$, pH 9.5-10.5. The temperature optimum was determined by assaying the enzyme activity in 25 mM Tris-HCl, pH 8.0 at temperatures ranging from 25° C. to 70° C.

Temperature stability of the enzyme. The thermal stability of the enzyme was determined by incubating the enzyme at various temperatures for 30 mM prior to activity determinations. Studies of the stability during storage were performed at 4° C. or −80° C. with or without additives. The additives were 0.2 mM of dithiothreitol (DTT), 10% ethylene glycol, 25% glycerol and 25% polyethylene glycol (PEG) 4000. The activity was checked every two weeks, as described above.

Metal chelator effects. Purified protein was incubated at room temperature with 5 mM 1,10-phenanthroline, 8-hydroxyquinoline-5-sulfonic acid, or ethylenediaminetetraacetic acid (EDTA) for 24 hours. PD-10 desalting columns (GE Healthcare) were used, as per the manufacturer's instructions, to remove the chelator from the enzyme. Enzymatic activity was measured with cyanuric acid as substrate, as described above.

Effects of metals. Enzyme was incubated with 0.2 mM of each metal salt for 60 min at 4° C. For each treatment, specific activity was determined, as described above. The final metal concentration in the assay buffer was 0.1 mM. The metals tested were CoCl$_2$, MnSO$_4$, NiCl$_2$, CuCl$_2$, ZnSO$_4$, FeCl$_3$, and FeSO$_4$. The following salts were also tested at the final concentrations indicated: 1 mM CaCl$_2$ and 2 mM MgCl$_2$.

Metal analysis. Enzyme was hydrolyzed with 6M hydrochloric acid at 110° C. for 24 hrs under vacuum. Metal content and protein concentrations were determined as previously described (de Souza, M. L., et al., 1996. *J. Bacteriol.* 178: 4894-4900).

Results

Figure 2:
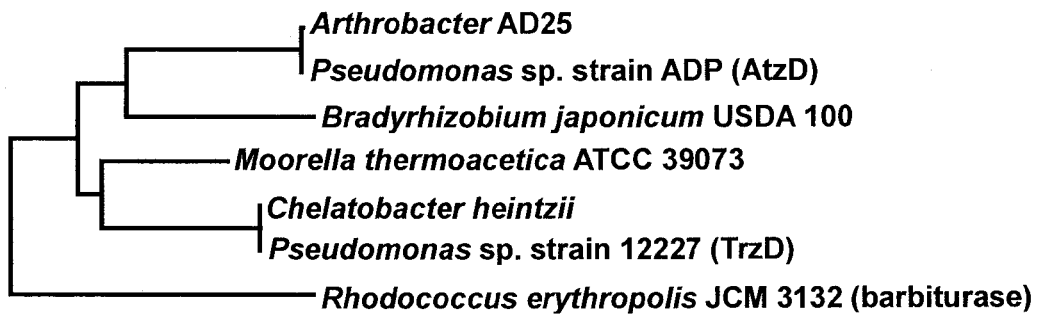
FIG. 2. Tree showing relatedness of cyanuric acid hydrolases known or identified in different bacteria. The degree of relatedness shown is based on amino acid sequence identity.

Identification of ORF Moth_2120. The BLAST algorithm was used to search GenBank for amino acid sequences homologous to AtzD, TrzD, and barbiturase. A subgroup of the sequences identified were found to cluster most closely to the cyanuric acid hydrolases (FIG. 2). The protein from *Chelatobacter heintzii* was identical to TrzD, and the protein from *Arthrobacter* AD25 was 99% identical to AtzD. The protein from *Bradyrhizobium japonicum* USDA 110 was 56%, 66%, and 44% identical to TrzD, AtzD, and barbiturase, respectively. A predicted protein sequence derived from the genome sequence of *Moorella thermoacetica* ATCC 39073 (gi83590946; locus tag Moth_2120) was 64%, 57%, and 48% identical to TrzD, AtzD, and barbiturase, respectively. This revealed two divergent homologs to known cyanuric acid hydrolases, but the known ability of *M. thermoacetica* to grow at elevated temperatures made this protein more attractive for further study.

Protein characterization and determination of catalytic activity. The putative cyanuric acid hydrolase homolog encoded by ORF Moth_2120 from *M. thermoacetica* ATCC 39073 was cloned and expressed in *E. coli* as described above. The resultant *E. coli* strain, unlike the wild-type strain, showed clearing zones on agar plates containing a suspension of 130 mM cyanuric acid. The recombinant protein was expressed with an N-terminal His-tag that allowed its purification to homogeneity in a single step. SDS-PAGE showed a single protein band corresponding to 40 kDa. This agrees with the calculated molecular weight of 38.9 kDa for a polypeptide encoded by this ORF.

The purified enzyme in vitro hydrolyzed cyanuric acid with a specific activity of 15.7 μmol/min/mg but did not show detectable activity with barbituric acid, even with the use of 50 μg of protein in a single assay. These results indicate that ORF Moth_2120 is a cyanuric acid hydrolase. Consistent with this view, the enzyme showed a physiologically reasonable $K_m$ value of 110 μM with cyanuric acid as substrate. The $k_{cat}$ was determined to be 10.6 s$^{-1}$ with a $k_{cat}/K_m$ of 1.0 10$^5$ M$^{-1}$s$^{-1}$. This compares with the published values for $K_m$ and $k_{cat}$ of 57 μM and 6.8 s$^{-1}$ for AtzD (7), and 50 μM and 250 s$^{-1}$ for TrzD (Smith, D., S. Alvey, and D. E. Crowley. 2005. *FEMS Microbiol Ecol.* 53:265-73).

Substrate specificity. Seventeen compounds that are structurally analogous to cyanuric acid were tested as substrates for hydrolysis by the *Moorella* cyanuric acid hydrolase (FIG. 3). Of these, only methyl isocyanurate was a substrate, with a rate of 0.13 μmol/min/mg, slightly less than 1% of the rate of the preferred substrate cyanuric acid. Based on these analyses, the substrates for this enzyme appear to require three nitrogen atoms in a six member ring as typical of s-triazine compounds, three carbonyl oxygen atoms on the carbons of the ring, and at least two of the ring nitrogens having hydrogens, while the other nitrogen atom can be bonded to a hydrogen or a methyl group.

Optimum pH and temperature of the enzyme. The activity for cyanuric acid hydrolase from *M. thermoacetica* ATCC 39073 was determined at pH values ranging from 5.5 to 10.5. Maximum activity was achieved at pH 8.0. This pH optimum agrees with the other characterized cyanuric acid hydrolases (Fruchey, I., N. et al., 2003. *Appl Environ Microbiol.* 69:3653-7; Smith, D., S. Alvey, and D. E. Crowley. 2005. *FEMS Microbiol Ecol.* 53:265-73). The effects of temperature on enzyme activity were also determined in the range of 25-70° C. The activity of the enzyme steadily increased with temperature, reaching a maximum at 70° C. of 24 μmol per min per mg protein. Temperatures greater than 70° C. could not be assayed due to the limitations of our equipment. The optimum temperature over this range was 70° C., which is much higher than the 45-50° C. range reported for TrzD (Smith, D., S. Alvey, and D. E. Crowley. 2005. *FEMS Microbiol Ecol.* 53:265-73).

Figure 4:
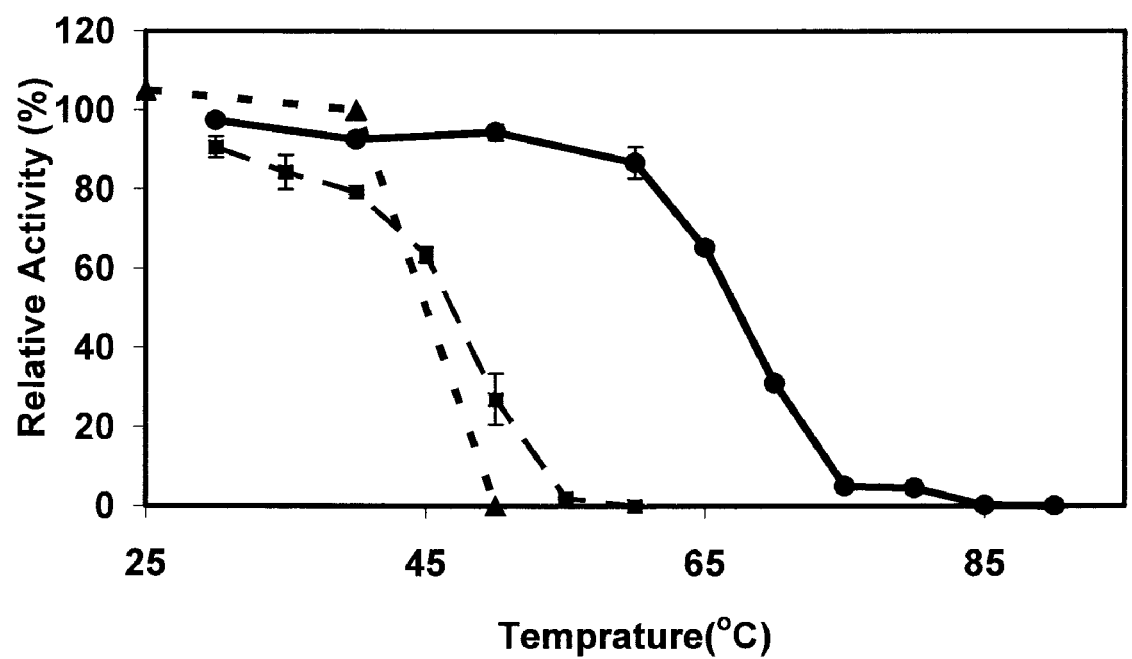
FIG. 4. Stability of enzyme activity vs. temperature at pH 8.0 for purified cyanuric acid hydrolases from *M. thermoacetica* ATCC 39073 (●) compared with TrzD (■) and AtzD (▲). Enzymes were maintained at the temperature indicated for 30 minutes prior to assay under standard conditions.
Figure 5:
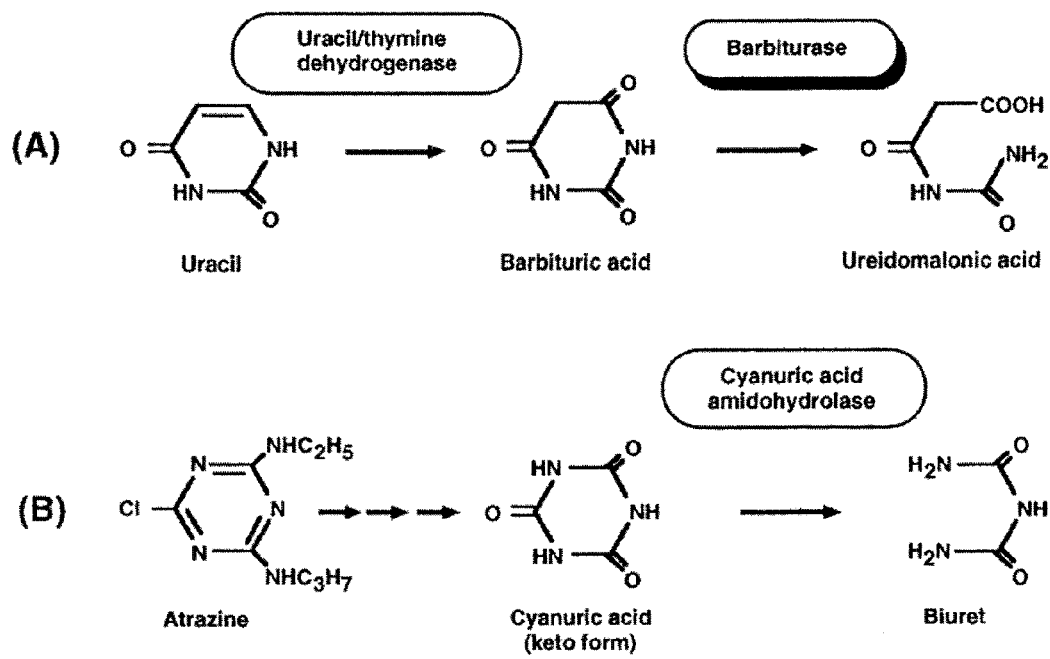
FIG. 5. Comparative reaction and metabolic pathways for barbiturase (A) and cyanuric hydrolase (B) (Soong, C. L., J. Ogawa, E. Sakuradani, and S. Shimizu. 2002. Barbiturase, a novel zinc-containing amidohydrolase involved in oxidative pyrimidine metabolism. J. Biol. Chem. 277:7051-7058).

Temperature stability of the enzyme. The thermostability of the enzyme at pH 8.0 was also tested by incubating the enzyme for 30 min prior to determining the activity (FIG. 4). At 50° C., 95% of initial activity remained with the *Moorella* enzyme, while at 70° C., 30% of the initial activity remained This contrasts with other members of this family of proteins. AtzD had no loss of activity at 40° C., but all activity was lost when incubated at 50° C. Likewise, TrzD lost most of its activity when the temperature was increased to 50° C. (FIG. 4). Barbiturase is also thermally sensitive and reported to have no residual activity after a 30 min incubation at 55° C. (Soong, C. L., et al., 2002. *J Biol Chem.* 277:7051-8) (18). These results suggest that the *Moorella* cyanuric acid hydrolase is structurally and catalytically more stable than other members of this family of enzymes.

Storage stability of the enzyme at 4° C. and −80° C. in the presence and absence of various additives was also examined (Table 1).

TABLE 1

Storage stability of purified cyanuric acid hydrolase from M. thermoacetica ATCC 39073 at pH 8.0 as a function of time and additives[a].

| Temperature (° C.) | Additive | Activity (μmol per min per mg protein)[b] | | | | |
|---|---|---|---|---|---|---|
| | | 0 week | 2 week | 4 week | 6 week | 8 week |
| 4° C. | enzyme only | 11.9 ± 0.23 | 12.5 ± 0.2 | 15.9 ± 0.7 | 16.6 ± 0.9 | 16.9 ± 1 |
| | 10% ethylene glycol | 12.3 ± 1.2 | 13.8 ± 0.3 | 11.3 ± 0.3 | 10.5 ± 0.9 | 11.4 ± 0.6 |
| | 0.2 mM of DTT | 13.4 ± 0.9 | 15.3 ± 0.5 | 17.7 ± 0.7 | 14.8 ± 0.3 | 18.3 ± 0.6 |
| | 25% glycerol | 14.3 ± 1.9 | 13.4 ± 0.1 | 12.2 ± 0.5 | 9.8 ± 0.5 | 12.0 ± 1.3 |
| | 25% PEG 4000 | 31.8 ± 1.8 | 20.0 ± 0.2 | 31.0 ± 0.5 | 22.2 ± 0.6 | 18.7 ± 0.1 |
| −80° C. | enzyme only | 11.9 ± 0.2 | 14.9 ± 0.1 | 14.3 ± 0.3 | 12.3 ± 0.4 | 11.7 ± 1.1 |
| | 10% ethylene glycol | 12.3 ± 1.2 | 13.3 ± 0.3 | 14.1 ± 0.3 | 13.6 ± 0.8 | 13.0 ± 0.2 |
| | 0.2 mM of DTT | 13.4 ± 0.9 | 14.7 ± 0.2 | 14.3 ± 0.3 | 12.2 ± 0.3 | 11.8 ± 0.3 |
| | 25% glycerol | 14.3 ± 1.9 | 14.0 ± 0.2 | 14.0 ± 0.9 | 10.7 ± 1.0 | 11.0 ± 1.2 |
| | 25% PEG 4000 | 31.8 ± 1.8 | 21.4 ± 0.7 | 22.0 ± 0.4 | 21.0 ± 0.3 | 17.1 ± 0.4 |

[a]Values are the mean ± standard error of three replicates.
[b]Activity was measured using the standard assay at 25° C.

Among the additives were 10% ethylene glycol, 0.2 mM DTT, 25% glycerol, and 25% PEG4000. The enzymatic activity was monitored every 2 weeks for a total of 8 weeks. The enzyme without additives showed no loss of activity after 8 weeks at both storage temperatures. This suggested that the enzyme was stable at low temperatures. Though the enzymatic activity was unchanged in the frozen sample after 8 weeks, the specific activity of the sample stored at 4° C. increased to 142% and 136% of initial specific activity compared to the sample without additives and 0.2 mM DTT, respectively. The addition of 25% PEG 4000 had a stimulatory affect upon activity prior to storage, increasing activity by 270%. However, activity for the PEG-stimulated enzyme subsequently decreased to around 1.4-1.6 times initial activity without additives over the 8 week time course at both temperatures. All other additives, including 10% ethylene glycol and 25% glycerol, had little or no positive effect on sustaining activity.

Effect of metal ions and chelators. The affects of divalent metals upon native enzyme activity were monitored (Table 2).

TABLE 2

Effect of metal ions on the activity of purified cyanuric acid hydrolase from M. thermoacetica [a]

| Metal | Concentration (mM) | Relative activity |
|---|---|---|
| $CoCl_2$ | 0.2 | 92 ± 5 |
| $MnSO_4$ | 0.2 | 96 ± 3 |
| $ZnSO_4$ | 0.2 | 51 ± 4 |
| $CuCl_2$ | 0.2 | 83 ± 3 |
| $FeCl_3$ | 0.2 | 105 ± 4 |
| $NiCl_2$ | 0.2 | 79 ± 3 |
| $CaCl_2$ | 1.0 | 121 ± 7 |
| $MgCl_2$ | 2.0 | 119 ± 2 |

[a] Values are the mean ± standard error of three replicates.

Zn(II) had the greatest inhibitory affect, with slight decreases in activity observed in the presence of Cu(II) and Ni(II). At higher concentrations, Ca(II) and Mg(II) caused slight increases to 121% and 119% of native activity, respectively. Chelators, including EDTA, o-phenanthroline, and 8-hydroxyquinoline-5-sulfonic acid, even with 24 h incubations, failed to alter activity. These data suggested that either a metal could not be removed or that metals were not necessary for catalytic activity.

Quantitation of bound metal. The metal content of the enzyme was analyzed by ICP. The only metals detected above background were zinc and nickel which were present at 0.08 and 0.05 molar metal to subunit stoichiometries, respectively. These results indicated that no catalytically-significant metals were present in the enzyme preparation having a $k_{cat}/K_m$ of $1.0 \times 10^5$ $M^{-1}s^{-1}$, a significant catalytic rate. Similar results were obtained with AtzD (Fruchey, I., et al., 2003. *Appl Environ Microbiol.* 69:3653-7).

Discussion

The cyanuric acid hydrolase enzymes AtzD from *Pseudomonas* sp. strain ADP (Fruchey, I., et al., 2003. *Appl Environ Microbiol.* 69:3653-7) and TrzD from *Pseudomonas* sp. strain NRRLB-12227 (Smith, D., S. Alvey, and D. E. Crowley. 2005. *FEMS Microbiol Ecol.* 53:265-73) have been purified and characterized. These enzymes were identified in organisms isolated for their ability to degrade atrazine and melamine, respectively. Both organisms mineralize the compounds via metabolic pathways that proceed through cyanuric acid as an intermediate. Cyanuric acid also forms abiotically via the spontaneous decomposition of chlorinated isocyanuric acids (Cantú, R., et al., 2000. *Anal. Chem.* 72:5820-8). The breakdown is an intended process as it serves to disinfect pools by slowly generating hypochlorite. After a time, however, cyanuric acid accumulates, rendering further chlorination ineffective. Various methods to remove cyanuric acid chemically have been tried, but none have proven commercially successful to date. To deal with this issue, enzymatic treatment of cyanuric acid in pool water has been considered. One impediment to this application has been the relative instability of the cyanuric acid hydrolases known to date.

The known cyanuric acid hydrolases, AtzD and TrzD, have been observed to lose activity during freezing, a typical method used to maintain enzyme stability and deter microbial and proteolytic breakdown of proteins. The goal of this study was to identify a more stable cyanuric acid hydrolase enzyme for use in bioremediation applications. In this context, the inventors identified an AtzD/TrzD homolog from *M. thermoacetica* ATCC 39073. This is the first cyanuric acid hydrolase purified from an organism not previously shown to degrade s-triazine compounds. Genome context gives little indication of a native function for this gene. Upstream of Moth_2120 are genes that encode for a CdaR transcriptional regulator, two hypothetical proteins, an FdrA protein implicated in regulating diverse cellular processes through FtsH, and another hypothetical protein. Downstream there is a hypothetical protein, uracil-xanthine permease, carbamate kinase, and methyltransferase genes.

The AtzD gene homolog from *M. thermoacetica* was cloned, the recombinant enzyme was purified. Characteristics of the enzyme were studied with respect to catalysis and stability. Table 3 compares the properties of this new enzyme with those of AtzD and TrzD.

TABLE 3

Comparison of Cyanuric Acid Hydrolases

| Properties | *Moorella* | TrzD | AtzD |
|---|---|---|---|
| Mol. wt. (calc.) (kDa) | 38.9 | 39.4 | 38.2 |
| pH optimum | 8.0 | 8.0-8.5(8) | 8.2(7) |
| Temp, optimum (° C.) | 70 | 45-50(8) | 30(6) |
| Thermostability$^a$ (° C.) | 20-65 | 20-45 | 20-40 |
| $k_{cat}$ (s$^{-1}$) | 10.6 | 250(8) | 6.8 ± 0.7(7) |
| $K_M$ (μM) | 110 | 50(8) | 57 ± 10(7) |
| $k_{cat}/K_M$ (s$^{-1}$M$^{-1}$) | $1.0 \cdot 10^5$ | $5 \cdot 10^6$ | $1.2 \cdot 10^5$ |
| Known substrates | Cyanuric acid, N-methylisocyanuric acid | Cyanuric acid(8) | Cyanuric acid, N-methylisocyanuric acid(7) |
| Metal content | None | n.d. | None(7) |
| Metal affects on activity | Cu(II), Zn(I), Ni(II) inhibitory at 0.2 mM; Ca(II), Mg(II) slight increase at 1.0 and 2.0 mM, respectively | Mg(II), Mn(II) no affect 1 mM; Co(II), Cu(II), Fe(II) slight inhibitory 1 mM; Zn(II) 1 mM greatly inhibitory(8) | No stimulatory affects with Zn(II), Cu(II), Fe(II), Co(II), or Ni(II)(7) |
| Influence of chelators on activity | No affect EDTA, o-phenanthroline, or 8-hydroxyquinoline-5-sulfonic acid | No affect EDTA(8) | No affect EDTA and o-phenanthroline |

$^a$Temperature where activity above 50% after a 30 min incubation.
n.d. = not determined The cyanuric acid hydrolase from *M. thermoacetica* ATCC 39073 was shown to have cyanuric acid hydrolase activity, with $K_m$ and $k_{cat}$ values for cyanuric acid of 110 μM and 10.6 s$^{-1}$, respectively. The enzyme displayed a high degree of substrate discrimination, only catalyzing reactions with cyanuric acid and its close structural analog N-methylisocyanuric acid, but with no other analogous structure. This mirrors the restricted reactivity found with AtzD (Fruchey, I., et al., 2003. *Appl Environ Microbiol.* 69:3653-7) and indicates that, although the sequences of the cyanuric acid hydrolases are only 57-64% identical, the proteins share a similar substrate range. The key difference between the *M. thermoacetica* cyanuric acid hydrolase and AtzD/TrzD is in the greater stability of the former enzyme. The new enzyme had its highest catalytic activity at 70° C. (the highest temperature that our assays were able to maintain), was stable when stored for 30 min at 50° C., and was able to be stored frozen for long periods of time. In combination, these properties make this a superior enzyme for cyanuric acid remediation.

Barbiturase, a cyanuric acid homolog, has been proposed to be a member of the amidohydrolase superfamily (Soong, C. L., et al., 2002. *J Biol Chem.* 277:7051-8). In general, amidohydrolase superfamily members contain one or two metal atoms per subunit, with zinc being the most commonly identified metal. The enzymes AtzA, AtzB, AtzC and TrzN, which are in the pathway of atrazine degradation, are all metalloenzymes and members of this superfamily (Seffernick, J. L., et al., 2007. *J Bacteriol.* 189:6989-97; Seffernick, J. L., et al., 2002. *Biochemistry* 41:14430-7; Shapir, N., et al., 2002. *J. Bacteriol.* 184:5376-84; Shapir, N., et al., 2006. *J Bacteriol.* 188:5859-64). However, sequence analysis of the AtzD/TrzD/barbiturase family of proteins revealed that they are not members of this common superfamily. Instead, these enzymes are very distant from any other proteins of known function, and cluster as an isolated island in sequence space. Because of the lack of sequence and evolutionary links to other well-characterized amidase enzymes, this family must be considered independently. Consistent with this, a metal was not necessary for catalysis by the *M. thermoaceticum* cyanuric acid hydrolase. Previously, active AtzD was found not to contain significant levels of metals (Fruchey, I., N. et al., 2003. *Appl Environ Microbiol.* 69:3653-7).

In conclusion, the cyanuric acid hydrolase from *M. thermoacetica* ATCC 39073 is not a metalloenzyme. Furthermore, it is an outstanding thermophilic enzyme that is stable at high or low temperatures.

EXAMPLE 2

Defining the Cyanuric Acid Hydrolase/Barbiturase Protein Family

As sequence databases grown and alignment methods become more sophisticated, many protein superfamilies have swelled to include tens or hundreds of thousands of members. Dozens of those members typically have available X-ray structures. This provides structure and function information that newly discovered members of the superfamily can be anchored to and thus provide immediate clues as its structure. A notable exception to this paradigm is the small cluster of related sequences that belong to proteins known to be, or annotated as, cyanuric or barbituric acid hydrolases. These related proteins catalyze the opening of structurally analogous nitrogen heterocyclic rings (FIG. 1). The barbituric acid hydrolases, also known as barbiturases, react with a pyrimidine ring and carry out recycling of cytosine and uracil. The cyanuric acid hydrolases have been largely identified in bacteria that catabolize anthropogenic s-triazine ring compounds such as the herbicide atrazine, or the monomer melamine. The barbiturases and cyanuric acid hydrolases characterized to date do not show cross-reactivity with each other substrates; they are each quite specific.

In pairwise comparisons, the barbiturases and cyanuric acid hydrolases generally show 40-60% relatedness to each other. There are annotated proteins that show approximately 50% sequence relatedness to each of a known cyanuric acid hydrolase and a known barbiturase. Thus, it can be difficult to discern from sequence alone if a protein is a cyanuric acid hydrolase or a barbiturase. It also is possible that some of the annotated proteins catalyze a different reaction altogether.

In light of these issues, the current study sought to further define the cyanuric acid/barbiturase protein family. The total membership in this family to-date was defined. Bioinformatics initially delineated each protein as a cyanuric acid hydrolase, barbiturase, or an unknown function protein. Several proteins from diverse were purified to homogeneity and most were shown to have cyanuric acid hydrolase activity and were not active with barbituric acid. One protein was a barbiturase. Another protein was observed to be unreactive with any substrate tested. A previous study had suggested that barbiturase was a member of the amidohydrolase superfamily and thus was a metalloenzyme. The present study finds no sequence relatedness to the amidohydrolase superfamily and no evidence for the participation of metals in catalysis by any member of the cyanuric acid/barbiturase family of proteins.

Materials and Methods

Spectrophotometric assay for cyanuric acid degradation. The rate of cyanuric acid hydrolysis catalyzed by pure or partially purified enzyme preparation was determined by monitoring the disappearance of cyanuric at 220 nm over time. The spectrophotometer was blanked with 1 ml of 25 mM Tris-HCl, pH 8.0. Enzyme was added to create an absorbance of 0.05 to 0.4, and reblanked. To this solution, 1 µl of 0.15 M cyanuric acid was added. The observed extinction coefficient for cyanuric acid in this range is 5.654 A220 nm/mM. When 25 mM Tris-HCl, pH 8.25 was used, the extinction coefficient for cyanuric acid was 5.848 A220 nm/mM. The absorbance of cyanuric acid was monitored over time and used to calculate the activity of the enzyme.

Preparation of soluble crude extract. E. coli was grown overnight at 30° C. with shaking at 225 rpm in 1 L LB broth containing 50 µg/ml ampicillin. Isopropyl-1-thio-B-D-galactoside (IPTG) was added to a final concentration of 1 mM when the culture reached OD600 nm 0.5. Cells were harvested by centrifugation at 5000×g for 15 minutes at 4° C., washed with 500 ml sterile PBS, and resuspended in 40 ml 25 mM MOPS, pH 7.0. The cells were lysed by one passage through a cold French pressure cell at 18,000 lb/in2. The extract was clarified initially by centrifugation at 13,000×g for 15 minutes at 4° C., followed by centrifugation at 25,000×g for 90 minutes at 4° C. This supernatant was designated the crude, cell-free soluble enzyme fraction and was used for further enzyme purification.

Results

The subunit sizes of the different cyanuric acid/barbiturase homologs were typically 350-380 amino acids with a molecular weight of approximately 40,000. The polypeptides are generally acidic with pI values in the range of 5-6.

The $k_{cat}$ and $K_m$ values for the cyanuric acid hydrolases are within an order of magnitude of each other. $K_{cat}$ ranges from 5-73 s$^{-1}$ and the $K_m$ from 19-58 µM. These give $k_{cat}/K_m$ in the range of $10^5$ to $10^6$. These values suggest that cyanuric acid hydrolysis is the true physiological function of these enzymes.

TABLE 4

Kinetic Properties of Cyanuric Acid Hydrolases

| Organism | $k_{cat}$ (s$^{-1}$) | $K_m$ (µM) | $k_{cat}/K_m$ (s$^{-1}$M$^{-1}$) |
|---|---|---|---|
| TrzD (literature) | 250 | 50 | 5 10$^6$ |
| TrzD (current study) | 14.2 ± 0.4 | 58 ± 7 | 2.5 10$^5$ |
| Pseudomonas sp. ADP -AtzD (literature) | 6.8 ± 0.7 | 57 ± 10 | 1.2 10$^5$ |
| Pseudomonas sp. ADP -AtzD (current study) | 73 ± 6 | 23 ± 7 | 3.2 10$^6$ |
| Moorella thermoacetica ATCC 39073 (literature) | 10.6 | 110 | 1.0 10$^5$ |
| Bradyrhizobium japonicum USDA 110 | 9.3 ± 0.7 | 50 ± 10 | 1.9 10$^5$ |
| Rhizobium leguminosarum bv. viciae 3841 | 5 ± 1 | 130 ± 60 | 3.8 10$^4$ |
| Methylobacterium sp. 4-46 | 17 ± 2 | 69 ± 16 | 2.5 10$^5$ |

Note:
All enzymes in the current study were stored at 4° C. and never frozen. Stability was monitored to ensure no deactivation occurred throughout the study.

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An isolated or purified structurally stable cyanuric acid hydrolase (CAH) enzyme having at least 95% sequence identity with the amino acid sequence SEQ ID No. 3.

2. The CAH of claim 1 having a $K_m$ value for cyanuric acid of 25-150 μM.

3. The CAH of claim 1 having a $k_{cat}$ value for cyanuric acid of 4.8-76 $s^{-1}$.

4. The CAH of claim 1, wherein the enzyme is thermostable.

5. The CAH of claim 1, wherein the enzyme retains at least 30% enzymatic activity at a temperature above 25° C.

6. The CAH of claim 1, wherein the enzyme has a pI of about 5-6.

7. The CAH of claim 1, wherein the enzyme is from *Moorella thermoacetica*.

8. The CAH of claim 7, wherein the enzyme is from *Moorella thermoacetica* ATCC 39073.

9. The CAH of claim 1, wherein the enzyme has a specific activity of 12-18 μmol/min/mg with cyanuric acid as substrate and less than 2 μmol/min/mg with barbituric acid as substrate.

10. A composition for remediation of a liquid comprising the CAH of claim 1 and polyethylene glycol (PEG) and/or KCl.

11. The composition of claim 10, wherein the PEG is PEG4000.

12. The composition of claim 10, wherein the PEG is present at a concentration of 5-50% by weight.

13. The composition of claim 10, wherein KCl is present at a concentration of 50-500 mM.

14. The composition of claim 10, wherein the liquid is water.

15. A device for remediation of a liquid comprising a matrix and the stable cyanuric acid hydrolase of claim 1.

16. The device of claim 15, wherein the device further comprises a casing or housing for the matrix, wherein water flows through the at least one casing and contacts the enzyme.

17. The device of claim 15, further comprising a permeable layer.

* * * * *